(12) United States Patent
Yamaguchi

(10) Patent No.: US 7,786,281 B2
(45) Date of Patent: *Aug. 31, 2010

(54) PROTEIN-DEAMIDATING ENZYME, MICROORGANISM PRODUCING THE SAME, GENE ENCODING THE SAME, PRODUCTION PROCESS THEREFOR, AND USE THEREOF

(75) Inventor: Shotaro Yamaguchi, Norwich (GB)

(73) Assignee: Amano Enzyme Inc., Nagoya-shi (JP)

( * ) Notice: Subject to any disclaimer, the term of this patent is extended or adjusted under 35 U.S.C. 154(b) by 103 days.

This patent is subject to a terminal disclaimer.

(21) Appl. No.: 12/289,225

(22) Filed: Oct. 23, 2008

(65) Prior Publication Data

US 2009/0075337 A1    Mar. 19, 2009

Related U.S. Application Data

(60) Division of application No. 10/815,774, filed on Apr. 2, 2004, now Pat. No. 7,462,477, which is a division of application No. 09/727,769, filed on Dec. 4, 2000, now Pat. No. 6,756,221, which is a continuation-in-part of application No. 09/324,910, filed on Jun. 3, 1999, now Pat. No. 6,251,651.

(30) Foreign Application Priority Data

Jun. 4, 1998  (JP) ................... 10-173940
Dec. 3, 1999  (JP) ................... 11-345044

(51) Int. Cl.
C07H 21/04    (2006.01)
C12N 9/80     (2006.01)
C12P 21/02    (2006.01)

(52) U.S. Cl. .................... 536/23.2; 435/228; 435/69.1

(58) Field of Classification Search ................ 536/23.2; 435/228, 69.1

See application file for complete search history.

(56) References Cited

U.S. PATENT DOCUMENTS 3,796,633 A    3/1974   Kikuchi et al.
5,082,672 A    1/1992   Hamada et al.
6,251,651 B1   6/2001   Yamaguchi et al.

FOREIGN PATENT DOCUMENTS

EP    0976829       2/2000
WO    WO-97/43910   11/1997

OTHER PUBLICATIONS

Vaintraub et al., Protein Deamidase from Germinating Wheat Grains, FEBS LETTS vol. 302, No. 2 (May 1992), pp. 169-171.

(Continued)

*Primary Examiner*—Karen Cochrane Carlson
*Assistant Examiner*—Rosanne Kosson
(74) *Attorney, Agent, or Firm*—Edwards Angell Palmer & Dodge LLP

(57) ABSTRACT

A method for the production of an enzyme, which comprises culturing in a medium a strain that belongs to a bacterium classified into *Cytophagales* or *Actinomycetes*, or a new bacterium *Chryseobacterium* sp. No. 9670 belonging to the genus *Chryseobacterium*, and has the ability to produce an enzyme having a property to deamidate amido groups in protein, thereby effecting production of the enzyme, and subsequently collecting the enzyme from the culture mixture and a method for the modification of protein making use of a novel enzyme which directly acts upon amido groups in protein, as well as a gene which encodes the enzyme, a recombinant vector which contains the gene, a transformant transformed with the vector and a method in which the transformant is cultured in a medium to effect production of the protein-deamidating enzyme and then the protein-deamidating enzyme is collected from the culture mixture. It is possible to provide a novel protein-deamidating enzyme which has an activity to release side chain carboxyl groups and ammonia from a protein by acting upon side chain amido groups in the protein, a microorganism capable of producing the same, a gene encoding the same, a production process therefor and use thereof.

8 Claims, 4 Drawing Sheets

OTHER PUBLICATIONS

Yamaguchi et al., A Novel Protein-Deamidating Enzyme from Chryseobacterium Proteolyticum Sp. Nov., a Newly Isolated Bacterium from Soil, Appl. Environ. Microbiol. vol. 66, No. 8, (Aug. 2000), pp. 3337-3343.

Hamada et al., Preparation and Functional Properties of Enzymatically Deamidated Soy Proteins, J. Food. Sci. vol. 54, No. 3, (May 1989), pp. 598-601, 635.

Database WPI, Section Ch, Week 199922, Derwent Publications Ltd., London, GB; Class B04, AN 1999-257687, XP002162641 & JP 11 075835 (Amano Pharm KK), Mar. 23, 1999 *abstract*.

Vinogradov et al., Prikladnaya Biokhimiya i Mikrobiologiya, 1976, 12(5); 704-8. Abstract only (in Russian w/ English abstract).

US 7,786,281 B2

PROTEIN-DEAMIDATING ENZYME, MICROORGANISM PRODUCING THE SAME, GENE ENCODING THE SAME, PRODUCTION PROCESS THEREFOR, AND USE THEREOF

PRIORITY INFORMATION

This is a divisional application of application Ser. No. 10/815,774, filed Apr. 2, 2004, (now U.S. Pat. No. 7,462,477), which is a divisional application of application Ser. No. 09/727,769, filed Dec. 4, 2000, (now U.S. Pat. No. 6,756,221), which is a Continuation-In-Part Application of U.S. application Ser. No. 09/324,910, filed Jun. 3, 1999 (now U.S. Pat. No. 6,251,651); the above noted prior applications are all hereby incorporated by reference. This application also claims priority to Japanese Application Nos. 10-173940, filed on Jun. 4, 1998, and 11-345044, filed on Dec. 3, 1999.

FIELD OF THE INVENTION

This invention relates to a novel enzyme, namely a novel enzyme which acts upon side chain amido groups in protein and thereby releases side chain carboxyl groups and ammonia, to a production process thereof and to a novel bacterium which produces the same. Particularly, it relates to a method for the production of an enzyme having a property to deamidate amido groups in protein, which comprises culturing a bacterial strain capable of producing an enzyme having a property to deamidate amido groups in protein, that belongs to *Cytophagales* or *Actinomycetes*, more particularly to the genus *Chryseobacterium, Flavobacterium, Empedobacter, Sphingobacterium, Aureobacterium* or *Myroides*, in a medium, thereby allowing the strain to produce the enzyme, and subsequently collecting the enzyme from the culture mixture. More particularly, it relates to a method for the production of an enzyme having a property to deamidate amido groups in protein, which comprises culturing a new strain *Chryseobacterium* sp. No. 9670 that belongs to the genus *Chryseobacterium*, thereby allowing the strain to produce the enzyme, and subsequently collecting the enzyme from the culture mixture. The invention also relates to a method for the modification of protein, which uses a novel enzyme having an activity to directly act upon amido groups in protein. It also relates to an enzyme which has a property to deamidate amido groups in protein, to a gene which encodes the enzyme, to a vector which contains the gene, to a transformant transformed with the vector, and to a method for the production of an enzyme having a property to deamidate amido groups in protein, which comprises culturing the transformant in a medium, thereby allowing the transformant to produce the enzyme, and subsequently collecting the enzyme from the culture.

BACKGROUND ART

Glutaminase and/or asparaginase are enzymes which hydrolyze glutamine and/or asparagine to convert them into glutamic acid and/or aspartic acid and ammonia, and it is well known that these enzymes are obtained from animals, plants and microorganisms. However, these enzymes are enzymes which act upon glutamine and/or asparagine in a specific fashion and cannot deamidate glutamine and/or asparagine in a peptide. Much less, they cannot deamidate γ and/or β-amido groups of glutamine and/or asparagine in a protein having larger molecular weight than that of a peptide. Still less, they cannot act upon glutamine and/or asparagine bonded in a protein state.

Also, transglutaminase is known as an enzyme which acts upon amido groups existing in a peptide state. This enzyme catalyzes the reaction of introducing an amine compound into protein by covalent bonding or the reaction of cross-linking the glutamine residue and lysine residue of protein via ε-(γ-glutamyl)lysine-peptide bonding, using the amido group of peptide-bonded glutamine as an acyl donor and the amino group of the primary amine as an acyl acceptor. It is known that, when amine or lysine does not exists in the reaction system or blocked, water acts as an acyl acceptor and the glutamine residue in peptide is deamidated to become glutamic acid residue, but since this enzyme is basically an acyl group transferase as described above, cross-linking reaction occurs when allowed to act on a usual protein and the reaction to deamidate protein does not occur, so that this enzyme is different from the enzyme of the invention.

In addition, Peptide glutaminase I and peptide glutaminase II produced by *Bacillus circulans* are known as an enzyme which performs deamidation by acting upon glutamine bonded in peptide. It is known that the former acts on the glutamine residue existing at the C terminal of peptide and the latter acts on the glutamine residue existing in the peptide. However, these enzymes do not act upon a high molecular weight protein and acts only upon a low molecular weight peptide [M. Kikuchi, H. Hayashida, E. Nakano and K. Sakaguchi, *Biochemistry*, vol. 10, 1222-1229 (1971)].

Also, plural studies have been made to attempt to allow these enzymes (Peptide glutaminase I and II) to act upon a high molecular weight protein rather than a low molecular weight peptide, and it has been revealed that these enzymes do not act on a high molecular weight protein but act only on a protein hydrolysate peptide. Illustratively, Gill et al. have reported that each of Peptide glutaminase I and II does not act on milk casein and whey protein both in native form and denatured form. They also have reported that, as a result of studies on activities on protein hydrolysate, only Peptide glutaminase II acted only on peptide having a molecular weight of 5,000 or less (B. P. Gill, A. J. O'Shaughnessey, P. Henderson and D. R. Headon, *Ir. J. Food Sci. Technol.*, vol. 9, 33-41 (1985)). Similar studies were carried out by Hamada et al. using soy bean protein, and the result was consistent with the result by Gill et al. That is, it was reported that these enzymes showed deamidation percentage of 24.4 to 47.7% on soy bean peptide (Peptone), but did not substantially act on soy bean protein (0.4 to 0.8%) (J. S. Hamada, F. F. Shih, A. W. Frank and W. E. Marshall, *J. Food Science*, vol. 53, no. 2, 671-672 (1988)).

A series of these reports by Hamada et al. show data indicating that peptidoglutaminase derived from *Bacillus circulans* acts on protein though very slightly. On the other hand, Kikuchi et al. (M. Kikuchi, H. Hayashida, E. Nakano and K. Sakaguchi, *Biochemistry*, vol. 10, 1222-1229 (1971) and Gill et al. (B. P. Gill, A. J. O'Shaughnessey, P. Henderson and D. R. Headon, *Ir. J. Food Sci. Technol.*, vol. 9, 33-41 (1985)) have used the same enzyme derived from the same strain (*Bacillus circulans* ATCC 21590) and reported that this enzyme acts on low molecular weight peptide but does not act on protein. The present inventor has purified the peptidoglutaminase derived from *Bacillus circulans* ATCC 21590 and confirmed that the slight apparent deamidation activity on protein reported by Hamada et al. is based on the action the enzyme upon peptide formed by the protease contaminated in the peptidoglutaminase preparation.

There is a report suggesting the existence of an enzyme originating from plant seed, which catalyzes deamidation of protein (I. A. Vaintraub, L. V. Kotova and R. Shara, *FEBS Letters*, vol. 302, 169-171 (1992)). Although this report observed ammonia release from protein using a partially purified enzyme sample, it is clear that this report does not prove the existence of the enzyme disclosed in the invention based on the following reasons. That is, since a partially purified enzyme sample was used, absence of protease activity was not confirmed, and no change in molecular weight of substrate protein after the reaction was not confirmed, there remains a possibility that not one enzyme but plural enzymes such as protease and peptidase acted on protein to release glutamine and/or asparagine as free amino acids and ammonia was released by glutaminase and/or asparaginase which deamidate these free amino acids or a possibility that glutamine-containing low molecular weight peptide produced in a similar way is deamidated by a peptide.glutaminase-like enzyme. In addition, there is a possibility that deamidation occurred as a side-reaction by protease. In particular, it should be noted that this report clearly describes that a glutaminase activity which acted on free glutamine to release ammonia was present in the partially purified preparation used therein.

Accordingly, there is no report until now which confirmed the presence of an enzyme which catalyzes deamidation of high molecular weight protein, by purifying the enzyme as a single protein and isolating and expressing the gene encoding the same.

In general, when carboxyl groups are formed by deamidation of glutamine and asparagine residues in protein, negative charge of the protein increases and, as the results, its isoelectric point decreases and its hydration ability increases. It also causes reduction of mutual reaction between protein molecules, namely, reduction of association ability, due to increase in the electrostatic repulsion. Solubility and water dispersibility of protein sharply increase by these changes. Also, increase in the negative charge of protein results in the change of the higher-order structure of the protein caused by loosening of its folding, thus exposing the hydrophobic region buried in the protein molecule to the molecular surface. In consequence, a deamidated protein has amphipathic property and becomes an ideal surface active agent, so that emulsification ability, emulsification stability, foamability and foam stability of the protein are sharply improved.

Thus, deamidation of a protein results in the improvement of its various functional characteristics, so that the use of the protein increases sharply (e.g., Molecular Approaches to Improving Food Quality and Safety, D. Chatnagar and T. E. Cleveland, eds., Van Nostrand Reinhold, New York, 1992, p. 37).

Because of this, a large number of methods for the deamidation of protein have been studied and proposed. An example of chemical deamidation of protein is a method in which protein is treated with a mild acid or a mild alkali under high temperature condition. In general, amido groups of glutamine and asparagine residues in protein are hydrolyzed by an acid or a base. However, this reaction is nonspecific and accompanies cutting of peptide bond under a strong acid or alkali condition. It also accompanies denaturation of protein to spoil functionality of the protein.

Because of this, various means have been devised with the aim of limiting these undesired reactions, and a mild acid treatment (e.g., J. W. Finley, *J. Food Sci.*, 40, 1283, 1975; C. W. Wu, S, Nakai and W. D. Powie, *J. Agric. Food Chem.*, 24, 504, 1976) and a mild alkali treatment (e.g., A. Dilollo, I. Alli, C. Biloarders and N. Barthakur, *J. Agric. Food Chem.*, 41, 24, 1993) have been proposed. In addition, the use of sodium dodecyl sulfate as an acid (F. F. Shih and A. Kalmar, *J. Agric. Food Chem.*, 35, 672, 1987) or cation exchange resin as a catalyst (F. F. Shih, *J. Food Sci.*, 52, 1529, 1987) and a high temperature treatment under a low moisture condition (J. Zhang, T. C. Lee and C. T. Ho, *J. Agric. Food Chem.*, 41, 1840, 1993) have also been attempted.

However, all of these methods have a difficulty in completely restricting cutting of peptide bond. The cutting of peptide bond is not desirable, because it inhibits functional improvement of protein expected by its deamidation (particularly reduction of foam stability) and also causes generation of bitterness. Also, the alkali treatment method is efficient in comparison with the acid treatment method, but it has disadvantages in that it causes racemization of amino acids and formation of lysinoalanine which has a possibility of exerting toxicity.

On the other hand, some enzymatic deamidation methods have also been attempted with the aim of resolving these problems of the chemical methods. Namely, a protease treatment method under a high pH (pH 10) condition (A. Kato, A. Tanaka, N. Matsudomi and K. Kobayashi, *J. Agric. Food Chem.*, 35, 224, 1987), a transglutaminase method (M. Motoki, K. Seguro, A. Nio and K. Takinami, *Agric. Biol. Chem.*, 50, 3025, 1986) and a peptide glutaminase method (J. S. Hamada and W. E. Marshall, *J. Food Sci.*, 54, 598, 1989) have been proposed, but all of these three methods have disadvantages.

Firstly, the protease method cannot avoid cutting of peptide bond as its original reaction. As described in the foregoing, cutting of peptide bond is not desirable.

In the case of the transglutaminase method, it is necessary to chemically protect ε-amino group of lysine residue in advance, in order to prevent cross-linking reaction caused by the formation of isopeptide bond between glutamine and lysine, as the original reaction of the enzyme. When a deamidated protein is used in food, it is necessary to deamidate glutamine after protection of the ε-amino group with a reversible protecting group such as citraconyl group, to remove the protecting group thereafter and then to separate the deamidated protein from the released citraconic acid. It is evident that these steps sharply increase the production cost and are far from the realization.

In the case of the peptidoglutaminase method, on the other hand, since this enzyme is an enzyme which originally catalyzes only deamidation of low molecular weight peptide as described in the foregoing, its joint use with protease is inevitable, so that it causes problems of forming bitter peptide and reducing functionality (particularly foam stability) similar to the case of the protease method.

In consequence, though the reaction selectivity due to high substrate specificity of enzymes is originally one of the greatest advantages of the enzymatic method, which surpasses chemical and physical methods, it is the present situation that the enzymatic method cannot be put into practical use for the purpose of effecting deamidation of protein because of the absence of an enzyme which does not generate side reactions and is suited for the deamidation of high molecular weight protein.

Under such circumstances, an enzyme capable of deamidating protein without causing reduction of molecular weight of the protein has been called for in the field of food protein industry.

Accordingly, the inventor of the invention has established a screening method which can be applied broadly to the microbial world and, by the use of this method, succeeded in finding microorganisms which can produce an enzyme capable of deamidating protein without causing reduction of molecular weight of the protein broadly in the microbial world, and have accomplished the invention by carrying out culturing of the microorganisms and isolation and purification of the deamidating enzymes.

SUMMARY OF THE INVENTION

In view of the above, the present inventor has conducted intensive studies searching for an inexpensive microorganism as the source of an enzyme capable of directly acting upon amido groups which are bonded to protein and thereby effecting deamidation of the protein, and, as a result of the efforts, have established a screening method which can be applied broadly to microorganisms. The inventor has found that a new bacterial strain belonging to the genus *Chryseobacterium*, newly isolated from a soil sample, can produce an enzyme which exerts the deamidation function by directly acting upon amido groups in the bonded state in protein without cutting peptide bond and cross-linking protein molecules. Thereafter, the inventor has completed the invention by finding that protein deamidated by this enzyme obtained by the screening has excellent functionality. In this specification, an enzyme which has the aforementioned actions is called a "protein-deamidating enzyme".

The inventor has then isolated and purified the protein-deamidating enzyme, determined nucleotide sequence of a gene coding for the protein-deamidating enzyme and confirmed that the protein-deamidating enzyme can be produced using a transformant transformed with a vector containing the gene.

Accordingly, the invention provides a method for the production of a protein-deamidating enzyme, the protein-deamidating enzyme, a gene (i.e., polynucleotide) which encodes the protein deamidating enzyme, and the like, in particular:

(1) An enzyme which has an activity to deamidate amido groups in a protein.

(2) An enzyme which has an activity to deamidate amido groups in a protein by directly acting upon the amido groups without cutting peptide bonds and without cross-linking a protein.

(3) The enzyme as described in (1) or (2) above, wherein said enzyme is derived from a microorganism.

(4) A polypeptide which comprises a polypeptide having an activity to deamidate amido groups in protein and having the amino acid sequence of SEQUENCE NO. 6 shown in the Sequence Listing, wherein one or more of amino acid residues of the amino acid sequence may be modified by at least one of deletion, addition, insertion and substitution.

(5) A polypeptide which comprises a polypeptide having the amino acid sequence of SEQUENCE NO. 6 shown in the Sequence Listing.

(6) A nucleotide which encodes a polypeptide having an activity to deamidate amido groups in protein.

(7) A nucleotide which encodes a polypeptide having an activity to deamidate amido groups in protein by directly acting upon the amido groups without cutting peptide bonds and without cross-linking a protein.

(8) A nucleotide which comprises a nucleotide being selected from the following nucleotides (a) to (g) and encoding a polypeptide having an activity to deamidate amido groups in protein;

(a) a nucleotide which encode a polypeptide having the amino acid sequence of SEQUENCE NO. 6 shown in the Sequence Listing, (b) a nucleotide which encodes a polypeptide having the amino acid sequence of SEQUENCE NO. 6 shown in the Sequence Listing, wherein one or more amino acid residues of the amino acid sequence are modified by at least one of deletion, addition, insertion and substitution, (c) a nucleotide which has the nucleotide sequence of SEQUENCE NO. 5 shown in the Sequence Listing, (d) a nucleotide which has the nucleotide sequence of SEQUENCE NO. 5 shown in the Sequence Listing, wherein one or more bases of the nucleotide sequence are modified by at least one of deletion, addition, insertion and substitution, (e) a nucleotide which hybridizes with any one of the aforementioned nucleotides (a) to (d) under a stringent condition, (f) a nucleotide which has homology with any one of the aforementioned nucleotides (a) to (d), and (g) a nucleotide which is degenerate with respect to any one of the aforementioned nucleotides (a) to (f).

(9) A nucleotide which comprises a nucleotide encoding a polypeptide having the amino acid sequence of SEQUENCE NO. 6 shown in the Sequence Listing.

(10) A recombinant vector which contains the nucleotide of any one of (6) to (9) above.

(11) A transformant transformed with the recombinant vector of (10) above.

(12) A method for producing an enzyme having an action to deamidate amido groups in protein, which comprises culturing the transformant of (11) above, thereby allowing said transformant to produce an enzyme having an activity to deamidate amido groups in protein, and subsequently collecting the enzyme having an activity to deamidate amido groups in protein from the culture mixture.

(13) A recombinant polypeptide having an action to deamidate amido groups in protein, which is obtained by the method of (11) above by culturing the transformant and collecting the polypeptide from said culture mixture.

(14) A method for producing a novel enzyme, which comprises culturing a microorganism in a nutrient medium, thereby allowing said microorganism to produce a novel enzyme having an activity to deamidate amido groups in protein, and subsequently collecting said enzyme.

(15) A method for producing a novel enzyme having an activity to deamidate amido groups in protein, which comprises culturing a microorganism in a nutrient medium, thereby allowing the microorganism to produce a novel enzyme which has an activity to deamidate amido groups in protein by directly acting upon the groups without causing severing of peptide bond and cross-linking of protein, and subsequently collecting said enzyme.

(16) The production process according to (14) or (15) above, wherein the microorganism is a bacterium belonging to *Cytophagales* or *Actinomycetes*.

(17) The production process according to (14) or (15) above, wherein the microorganism is a bacterium belonging to Flavobacteriaceae.

(18) The production process according to (14) or (15) above, wherein the microorganism belonging to the genus selected from the group consisting of *Chryseobacterium, Flavobacterium, Empedobacter, Sphingobacterium, Aureobacterium* and *Myroides*.

(19) The production process according to (14) or (15) above, wherein the microorganism belonging to the genus *Chryseobacterium*.

(20) The production process according to (14) or (15) above, wherein the microorganism is a strain *Chryseobacterium* sp. No. 9670 (FERM BP-7351).

(21) A method for modifying a protein or a peptide, which comprises allowing an enzyme having an activity to deamidate amido groups in protein or peptide by directly acting upon the groups without causing severing of peptide bond and cross-linking of protein to react with a protein or a peptide.

(22) A composition for use in modification of a protein or a peptide, which comprises an enzyme having an activity to deamidate amido groups in protein or peptide by directly acting upon the groups without causing severing of peptide bond and cross-linking of protein, as the active ingredient.

(23) An isolated microorganism *Chryseobacterium* sp. No. 9670 (FERM BP-7351).

(24) A method for improving functionality of a plant or animal protein and/or peptide, which comprises allowing an enzyme having an activity to deamidate amido groups in protein and peptide by directly acting upon the groups without causing severing of peptide bond and cross-linking of protein to react with the protein and/or peptide.

(25) A method for improving functionality of food containing a plant or animal protein and/or peptide, which comprises allowing an enzyme having an activity to deamidate amido groups in protein and peptide by directly acting upon the groups without causing severing of peptide bond and cross-linking of protein to react with the food.

DETAILED DESCRIPTION OF THE INVENTION

Figure 1:
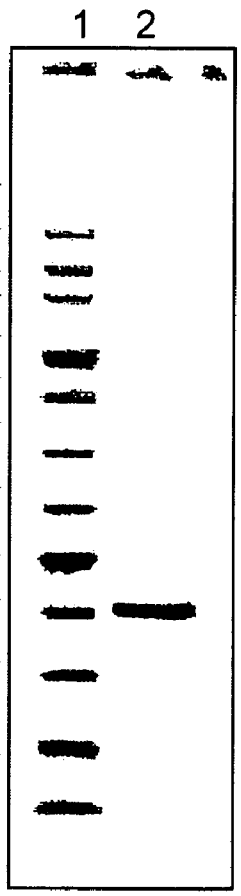
FIG. 1 is a graph showing results of SDS-polyacrylamide gel electrophoresis of the purified protein-deamidating enzyme of Example 6. Lane 1 shows molecular weight marker proteins and lane 2 is the purified protein-deamidating enzyme.

The protein-deamidating enzyme of the invention is effective on the amido group of at least asparagine residue or glutamine residue in protein, but its action site is not particularly limited, and it can be effective on the amido group connected to other amino acid residues. In this connection, the term "protein" as used herein is not limited to simple protein and it may also be protein complexes, e.g., with saccharides or lipids. Also, the molecular weight of the protein is not particularly limited and is generally 5,000 (50 residues) or more and preferably in the range of from 10,000 to 2,000,000.

The protein-deamidating enzyme of the invention can also be used for the deamidation of peptides having amido groups or derivatives thereof, in addition to proteins. Examples of the peptides include those generally having amino acid residues of from 2 to 50, and those which are used as nutrition-improving agents are preferable.

Thus, the protein-deamidating enzyme of the invention can use from dipeptides to high molecular weight proteins, including polypeptides, as its substrates. In this connection, the term "polypeptides" as used in this specification includes proteins.

A microorganism capable of producing the protein-deamidating enzyme of the invention can be screened, for example, in the following manner. That is, 1) an enrichment culturing is carried out by inoculating a microbial source such as a soil sample into a medium which contains Cbz-Gln-Gly as the sole nitrogen source, 2) next, the culture broth obtained in 1) is inoculated onto an agar medium which contains Cbz-Gln-Gly as the sole nitrogen source to obtain a grown strain, and then 3) the thus obtained strain is cultured in an appropriate liquid nutrient medium to check the activity in the culture broth to release ammonia from Cbz-Gln-Gly and casein.

Composition of the medium to be used in the enrichment culturing is optionally selected in response to the microorganism to be cultured, except that it contains Cbz-Gln-Gly as the sole nitrogen source, and culturing temperature and other various conditions are also optionally selected in response to the microorganism to be cultured. When the microorganism to be cultured is a bacterium, the medium described in Example 1 of the invention, for example, can be used, and when the microorganism to be cultured is a fungus or yeast, a medium in which nitrogen sources are removed from Czapex-Dox liquid medium (3% sucrose, 0.1% $K_2HPO_4$, 0.05% $MgSO_4 \cdot 7H_2O$, 0.05% KCl, 0.0001% $FeSO_4 \cdot 7H_2O$) or a modified SD medium (2% glucose, 0.17% Bacto Yeast Nitrogen base without amino acids and ammonium sulfate (Difco)) can be used in addition to the medium described in Example 1. Regarding the culturing for screening algae, it can be carried out in accordance, for example, with "Microalgae, biotechnology and microbiology" (Becker, E. W., pp. 9-46, 1993, Cambridge University Press, Cambridge, United Kingdom). Culturing with the nutrient medium in the above step 3) is carried out in the same manner. Selection and practice of these conditions do not require unnecessary, inadequate, broad and immoderate experiments for those skilled in the art.

When one of the strains obtained in this manner (strain No. 9670) was identified in accordance with Bergey's Manual of Determinative Bacteriology, it was identified as a species belonging to the genus *Chryseobacterium*. This strain was named *Chryseobacterium* sp. No. 9670 and deposited on Nov. 29, 1999 with accession number FERM P-17664 (transferred to FERM BP-7351 on Nov. 8, 2000) at National Institute of Bioscience and Human-Technology, Agency of Industrial Science and Technology, Japan of which address is 1-3, Higashi 1-chome, Tsukuba-shi, Ibaraki-ken, 305-8566, Japan.

The strain No. 9670 is a *Chryseobacterium* sp., because it is Gram negative, in rod shape, non-motile, aerobic, catalase positive and oxidase positive, and it forms an insoluble yellow to orange pigment.

REFERENCES (1) Vandamme, P., J.-F. Bernardet, P. Segers, K. Kersters and B. Holmes, 1994. New Perspective in the Classification of the Flavobacteria: Description of *Chryseobacterium* gen. nov., *Bergeyella* gen. nov., and *Empedobacter* nom. rev., *Int. J. Syst. Bacteriol.*, 44: 827-831.

(2) Holmes, B., R. J. Owen and T. A. McMeekin, 1984. Genus *Flavobacterium*, Bergey, Harrison, Breed, Hammer and Huntoon, 1923, $97^{AL}$, pp. 353-361. In N. R. Krieg and J. G. Holt (ed.), Bergey's manual of systematic bacteriology, vol. 1, The Williams & Wilkins Co., Baltimore.

I. Morphology

| Shape of cell: | rod |
|---|---|
| Gram staining: | negative |
| Motility: | negative |
| Spore formation: | negative |

II. Physiological Property

TABLE 1

| Items tested | Property |
|---|---|
| Reduction of nitrate | Negative |
| Denitrification | Negative |
| Formation of indole | Positive |
| Formation of hydrogen sulfide | Weakly positive (zinc acetate test paper method) |
| Hydrolysis of starch | Positive |
| Utilization of citrate: | |
| Simmons's citrate medium | Negative |
| Christensen's citrate medium | Positive |
| Formation of pigment | Forms insoluble yellow to orange pigment |
| Urease | Negative |
| Oxidase | Positive |
| Catalase | Positive |
| Growth at 37° C. | Positive |
| Growth at 42° C. | Negative |
| Behavior for oxygen | Aerobic growth but not anaerobic |
| O-F test | Oxidative formation of acid from glucose |
| Hydrolysis of casein | Positive |
| Hydrolysis of gelatin | Positive |
| Hydrolysis of DNA | Positive |
| Hydrolysis of esculin | Positive |
| Growth in McConkey's medium | Negative |
| VP reaction | Negative |
| Acid formation from saccharides: | |
| L-Arabinose | Positive (no gas formation) |
| D-Xylose | Weakly positive (no gas formation) |
| D-Glucose | Positive (no gas formation) |
| Maltose | Positive (no gas formation) |
| Sucrose | Positive (no gas formation) |
| Lactose | Negative |
| Trehalose | Positive (no gas formation) |
| D-Mannitol | Positive (no gas formation) |
| Inositol | Negative |
| Glycerol | Weakly positive (no gas formation) |
| Soluble starch | Positive (no gas formation) |

In this connection, this enzyme can be distinguished from known transglutaminase, because it does not have the activity to catalyze formation of isopeptide between glutamine residue and lysine residue in protein, namely transglutaminase activity. It can also be distinguished from known protease, because it does not have the activity to hydrolyze peptide bond of protein, namely protease activity.

Regarding the culturing method of the above strain for the production of the protein-deamidating enzyme, either a liquid culturing or a solid culturing, but preferably a liquid culturing, may be used. The liquid culturing can be carried out for example in the following manner.

Any medium can be used with the proviso that a microorganism capable of producing the protein-deamidating enzyme can grow in the medium. Examples of the medium to be used include those which contain carbon sources such as glucose, sucrose, glycerol, dextrin, molasses and organic acids, nitrogen sources such as ammonium sulfate, ammonium carbonate, ammonium phosphate, ammonium acetate, peptone, yeast extract, corn steep liquor, casein hydrolysate and beef extract and inorganic salts such as potassium salts, magnesium salts, sodium salts, phosphoric acid salts, manganese salts, iron salts and zinc salts.

The medium pH is adjusted to a value of approximately from 3 to 9, preferably from about 5.0 to 8.0, and the culturing is carried out under aerobic conditions at a temperature of generally from about 10 to 50° C., preferably from about 20 to 37° C., for a period of from 12 hours to 20 days, preferably from 1 to 7 days. As the culturing method, a shaking culture method or an aerobic submerged jar fermentor culture method may be used.

The protein-deamidating enzyme of the invention can be obtained by isolating the protein-deamidating enzyme from the thus obtained culture broth in the usual way. For example, when the protein-deamidating enzyme is isolated and purified from the culture broth, purified protein-deamidating enzyme can be obtained by treating it in the usual way by the combination of centrifugation, UF concentration, salting out and various types of chromatography such as of an ion exchange resin.

The invention is described more illustratively. That is, the aforementioned *Chryseobacterium* sp. No. 9670 was used as a protein-deamidating enzyme producing strain and cultured in a liquid medium, and production, purification and properties of the enzyme were examined.

One loopful of cells grown on a fresh slant medium were inoculated into LB Base medium (mfd. by Gibco) and cultured on a shaker at 25° C. for 2 to 7 days, and then centrifugation supernatant is obtained.

After completion of the culturing, the enzyme of interest was purified by subjecting the culture broth to centrifugation (12,000 rpm, 4° C., 20 minutes) to obtain the supernatant as a crude enzyme solution, and treating the thus obtained solution by UF concentration (SEP-0013), salting out, Phenyl-Sepharose and Sephacryl S-100. Steps of the purification are shown in Table 2.

TABLE 2

| | Total protein mg | Total activity U | Specific activity U/mg | Yield % | Purification degree |
|---|---|---|---|---|---|
| Culture filtrate | 3547.8 | 606.8 | 0.171 | 100 | 1.00 |
| UF Concentrate | 492.8 | 483.6 | 0.981 | 79.7 | 5.74 |
| Salting out | 404.3 | 383.5 | 0.949 | 63.2 | 5.55 |

TABLE 2-continued

|  | Total protein mg | Total activity U | Specific activity U/mg | Yield % | Purification degree |
|---|---|---|---|---|---|
| Phenyl-Sepharose | 35.83 | 255.5 | 7.13 | 42.1 | 41.7 |
| Sephacryl s-100 | 7.02 | 236.4 | 33.7 | 39.0 | 197.1 |

In this case, measurement of the enzyme activity was carried out in the following manner using Z-Gln-Gly and casein as substrates.

Activity measuring method: A 10 μl portion of each enzyme solution is added to 100 μl of 176 mM phosphate buffer (pH 6.5) containing 10 mM Z-Gln-Gly and incubated at 37° C. for 60 minutes, and then the reaction is stopped by adding 100 μl of 12% trichloroacetic acid solution. After centrifugation (15,000 rpm, 4° C., 5 minutes), the resulting supernatant is measured in the following manner using F-kit ammonia (mfd. by Boehringer-Mannheim) (A1). Separately, the same measurement is carried out using water instead of the enzyme solution (A2).

A 10 μl portion of the supernatant and 190 μl of water are added to 100 μl of the F-kit ammonia reagent 2, the resulting mixture is allowed to stand at room temperature for 5 minutes and then the absorbance of 100 μl portion of the reaction solution is measured at 340 nm (E1). The remaining 200 μl portion is mixed with 1.0 μl of reagent 3 (glutamate dehydrogenase), allowed to stand at room temperature for 20 minutes and then the absorbance of the remaining 200 μl is measured at 340 nm (E2).

The amount of enzyme which releases 1 μmol of ammonia within one minute under the above reaction conditions is defined as one unit and calculated based on the following formula.

$$U/ml=1.76\times[A1(E1-E2)-A2(E1-E2)]$$

Using 1% casein (Hamerstein, mfd. by Merck) instead of 10 mM Z-Gln-Gly as the substrate, the activity is measured in the same manner to confirm that the enzyme acts upon amino groups bonded to the protein. In this case, the protease activity was also checked by measuring the absorbance of the centrifugation supernatant after termination of the reaction at 280 nm. The amount of enzyme which increases 1 OD units under this condition was defined as one unit of protease activity.

Transglutaminase activity was measured by the following hydroxamic acid method using Z-Gln-Gly as the substrate.
Reagent A 0.2 M Tris-HCl buffer (pH 6.0)
0.1 M hydroxylamine
0.01 M reduced-type glutathione
0.03 M benzyloxycarbonyl-L-glutaminylglycine
Reagent B 3 N hydrochloric acid
12% trichloroacetic acid
5% $FeCl_3 \cdot 6H_2O$ (dissolved in 0.1 N HCl)
A 1:1:1 mixture of these solutions is used as reagent B.

A 0.05 ml portion of each enzyme solution is mixed with 0.5 ml of the reagent A to carry out 10 minutes of the reaction at 37° C., the reaction solution is mixed with 0.5 ml of the reagent B to stop the reaction and to effect formation of Fe complex, and then the absorbance at 525 nm is measured. As a control, the same reaction is carried out using the same enzyme solution heat-inactivated in advance, and the absorbance is measured to calculate its difference from the absorbance of the intact enzyme solution. Separately, a calibration curve is prepared using L-glutamic acid γ-monohydroxamate instead of the enzyme solution, for use in the calculation of the amount of formed hydroxamic acid based on the just described difference in absorbance, and the enzyme activity which forms 1 μmol of hydroxamic acid within one minute is defined as one unit.

In this connection, the amount of protein was determined using BCA Protein Assay Kit (mfd. by Pierce) and bovine serum albumin as the standard protein.

(1) Measurement of molecular weight: This was 20 kDa when measured by SDS-polyacrylamide gel electrophoresis (FIG. 1).

(2) Measurement of optimum pH: A 100 μl portion of 40 mM Britton-Robinson buffer solution (having a pH value of from 3 to 12) containing 10 mM Z-Gln-Gly was pre-incubated at 37° C. for 5 minutes, 10 μl of each enzyme solution containing 0.32 μg of the protein-deamidating enzyme was added to the buffer and incubated at 37° C. for 60 minutes to measure the enzyme activity. As the results, the optimum pH was around 6.

(3) Measurement of optimum temperature: A 10 μl portion of enzyme solution containing 1.21 μg of the protein-deamidating enzyme was added to 100 μl of a substrate solution [176 mM phosphate buffer (pH 6.5) containing 10 mM Z-Gln-Gly], and the reaction was carried out at each temperature for 60 minutes to measure the enzyme activity. As the results, the optimum temperature was around 60° C.

(4) Measurement of pH stability: A 22 μl portion of enzyme solution containing 0.75 μg of the protein-deamidating enzyme (in 40 mM Britton-Robinson buffer solution having a pH value of from 3 to 12) was treated at 30° C. for 18 hours. Thereafter, the remaining enzyme activity was measured. As the results, the enzyme was stable at approximately from pH 5 to 9.

(5) Measurement of temperature stability: A 43 μl portion of enzyme solution containing 1.76 μg of the protein-deamidating enzyme [in 50 mM phosphate buffer solution (pH 7.0)] was allowed to stand at each temperature for 10 minutes, and then the remaining enzyme activity was measured. As the results, the enzyme was stable at up to 50° C.

(6) Substrate specificity: Each solution of various proteins having a final concentration of 1% (50 mM phosphate buffer, pH 6.5) was used as the substrates and mixed with the protein-deamidating enzyme, and 1 hour of the reaction was carried out at 37° C. After the reaction, trichloroacetic acid solution was added to a final concentration of 6.4% to terminate the reaction, and the reaction mixture was centrifuged at 13,000 rpm for 3 minutes to measure amount of ammonia in the resulting supernatant. As a control, the same treatment was carried out by adding the enzyme after termination of the reaction, and amount of ammonia in the supernatant was measured. By subtracting the amount of released ammonia by the control test from the amount of ammonia released by the enzyme reaction test, the amount of ammonia released by the enzyme reaction was obtained to calculate ammonia releasing rate. The ammonia releasing rate was expressed as the amount of ammonia released by 1 mg of enzyme during 1 minute. The results are shown in Table 3. When a portion of the reaction mixture after completion of the reaction was subjected to SDS-PAGE and compared with the control, increased or decreased molecular weight of the protein was not found. This result means that the enzyme of the invention is a novel enzyme which can be distinguished from known transglutaminase and protease.

TABLE 3

| Protein | Ammonia releasing rate (μmole/min/mg ± SD[a]) |
| --- | --- |
| α-Casein, bovine milk | 19.12 ± 0.51 |
| β-Casein, bovine milk | 18.11 ± 0.15 |
| α-Lactoalbumin, bovine milk | 0.836 ± 0.009 |
| β-Lactoglobulin, bovine milk | 0.728 ± 0.001 |
| Bovine serum albumin, bovine | 0.009 ± 0.001 |
| Ovalbumin, chichen egg | 0.005 ± 0.002 |
| Gluten, wheat[b] | 7.200 ± 0.333 |
| Gliadin, what[b] | 5.473 ± 0.017 |
| Zein, corn[b] | 0.655 ± 0.176 |
| Soy protein isolate | 1.170 ± 0.064 |
| Collagen, Type I, bovine Achilles tendon[b] | 0.177 ± 0.017 |
| Gelatin, Type B, bovine skin | 0.696 ± 0.100 |
| Muscle acetone powder, chicken breast[b] | 0.210 ± 0.034 |
| Myoglobin, horse skeletal muscle | 0.014 ± 0.001 |
| Actin, bovine muscle | 0.450 ± 0.022 |
| RNase A, bovine pancreas | 2.912 ± 0.367 |
| α-Chymotrypsinogen A, bovine pancreas | 0.650 ± 0.118 |
| Aprotinin, bovine lung | 0.224 ± 0.064 |

(7) Measurement of isoelectric point: When measured by the electrofocusing Ampholine (600 V, 4° C., 48 hours), isoelectric point of this enzyme was 10.0.

Next, the method of the invention for the modification of protein using the protein-deamidating enzyme is described in detail.

The protein-deamidating enzyme of the invention is allowed to act upon various proteins. Any type of protein can be used, with the proviso that it undergoes action of the enzyme, and its examples are plant proteins obtained from beans and cereals and animal proteins which include milk proteins such as casein and β-lactoglobulin, egg proteins such as ovalbumin, meat proteins such as myosin and actin, blood proteins such as serum albumin and tendon proteins such as gelatin and collagen. Also included are partially hydrolyzed proteins obtained by chemical treatment with an acid or an alkali or by enzymatic treatment for example with a protease, chemically modified proteins with various reagents and synthesized peptides.

These substrate proteins are subjected to the reaction in the form of solution, slurry or paste, but their concentrations are not particularly limited and optionally selected depending on the desired properties and conditions of the deamidating protein of interest. Also, the solution, slurry or paste of each substrate protein is not limited to an aqueous solution and may be in the form of emulsion with oil and fat and, as occasion demands, may contain additives such as salts, saccharides, proteins, perfumes, moisture keeping agents and coloring agents.

The reaction conditions such as amount of the enzyme, reaction time and temperature and pH of the reaction solution are not particularly limited too, but the reaction may be generally carried out using the enzyme in an amount of from 0.1 to 100 units, preferably from 1 to 10 units, based on 1 g of protein, at a reaction temperature of from 5 to 80° C., preferably from 20 to 60° C., at a reaction solution pH of from 2 to 10, preferably from 4 to 8, and for a period of from 10 seconds to 48 hours, preferably from 10 minutes to 24 hours. In addition, these conditions can be optionally changed depending, for example, on the purity of the enzyme to be used and the kind and purity of the substrate protein to be used.

Thus, the action of the protein-deamidating enzyme of the invention upon various proteins renders possible direct deamidation of amido groups in the protein. As the results, negative charge of the thus deamidated protein increases which accompanies reduced pI, increased hydration ability and increased electrostatic repulsion. Also, changes in the higher-order structure of protein result in the increased surface hydrophobic property. These effects result in the improvement of functionality of protein, such as increased solubility and dispersibility, increased foamability and foam stability and increased emulsification ability and emulsification stability.

Thus, the protein having improved functionality greatly expands its use mainly in the field of food. A number of plant proteins show poor functionality such as solubility, dispersibility and emulsification ability particularly under weakly acidic condition which is the pH range of general food, so that they are limited in the use in many food articles which include acidic drinks such as coffee whitener and juice, dressing, mayonnaise and cream. However, when a plant protein having poor solubility, such as wheat gluten for example, is deamidated by the invention, its solubility and dispersibility are increased, so that its use in these unsuited food articles becomes possible and it can be used as tempura powder having high dispersibility.

The enzyme of the invention can also be used for the improvement of dough in the field of bakery and confectionery. For example, a dough having high gluten content has problems in terms of handling and mechanical characteristics of the dough because of its low extensibility, as well as volume and quality of the finished bread. These problems can be resolved by improving the extensibility through the deamidation of gluten with this enzyme. In addition, since the deamidated gluten shows the effect as an emulsifying agent, bread producing characteristics such as keeping quality and softness are also improved. Also, a dough containing deamidated gluten has low plasticity and excellent extensibility, so that this is suitable for the production of crackers, biscuits, cookies, pizza pies or crusts of pie, and the enzyme of the invention can be used in their production. For this purpose, the enzyme of the invention is used in an amount of from 0.01 to 10,000 units, preferably from 0.1 to 150 units, based on the total weight of dough comprised of wheat flour, water and the like materials which may be mixed in the usual way.

Still more, when a protein in food, which causes allergy, a non-resistant disease or a genetic disease, is treated with the enzyme of the invention, its toxicity and allergenic property can be removed or reduced. In the case of food allergy, most of the allergen peptides generally have high hydrophobic property. When they are converted into hydrophilic peptides by their treatment with the enzyme, the allergenic property is removed or reduced. Particularly, large effect can be obtained when an allergen peptide contains glutamine residue such as the case of a wheat gluten allergen.

Still more, when a protein is deamidated by this enzyme, mineral-sensitivity of the protein is reduced, so that the soluble mineral content in a protein-mineral solution is increased and absorption of minerals in the human body can be improved. It is well known in general that absorption of calcium contained in food by the human body is improved when calcium is solubilized using an organic acid or casein phosphopeptide. Based on the same mechanism, it is possible to solubilize a large quantity of calcium by deamidation of the protein by the enzyme of the invention. Using the deamidated protein, high mineral (e.g., calcium)-containing drinks and mineral (e.g., calcium) absorption enhancing agents can be produced.

Also, in the case of the production of amino acid based condiments (hydrolysate of animal protein (HAP) and hydrolysate of plant protein (HVP)), bean paste (miso) or soy sauce, other effects such as reduction of bitterness, improvement of protein hydrolyzing ratio by protease and increase in the glutamic acid content can be obtained. It is well known in general that the cause of bitterness is originated from hydrophobic peptides, so that the deamidation renders possible reduction of bitter peptides. It is known also that a peptide having glutamic acid on its N-terminal has the effect to mask bitterness. In addition, since primary structure and higher-order structure of a material protein are changed by deamidation, protease-sensitivity of the protein can also be increased. As the results, the low protein hydrolyzing ratio, as a problem involved in the enzymatic production of HAP and HVP, can also be improved. On the other hand, reduction of the glutamic acid content caused by the formation of pyroglutamic acid is another problem in the production of HAP and HVP. Pyroglutamic acid is formed by the intramolecular cyclization of free glutamine, but it can be prevented by deamidation of the material protein and, as the result, the glutamic acid content is increased.

Still more, the enzyme of the invention can be used as an agent for use in the control of the transglutaminase reaction. Transglutaminase is broadly used as a protein modifying agent, namely as a cross-linking enzyme, in the field of food and other industrial fields. The purpose of the use of transglutaminase is to obtain gelled protein products by the protein cross-linking reaction of the enzyme or to improve functionality of protein, but it is difficult to obtain a product having desired cross-linking degree and functionality in response to respective use and object, namely to control the cross-linking reaction such as termination of the reaction at an appropriate stage. Particularly in the case of the modification of proteins for food use, it is not desirable to add generally known transglutaminase inhibitors such as EDTA, ammonium chloride and SH reagents.

It is possible to terminate the transglutaminase reaction by adding the protein-deamidating enzyme of the invention at a desired stage during the reaction of transglutaminase. That is, the transglutaminase reaction can be stopped by converting glutamine residues which are the target of the transglutaminase reaction in the substrate protein into glutamic acid residues by the protein-deamidating enzyme.

In that case, it is necessary that the affinity of the protein-deamidating enzyme for glutamine residues in a protein as its substrate is higher than that of transglutaminase, but the latter case of reaction requires the ε-amino group of lysine in addition to glutamine residues while the former case requires only water other than the glutamine residues, which is abundantly present in the reaction environment, so that it can be assumed that the reaction of protein-deamidating enzyme generally precedes the reaction of transglutaminase. As a matter of course, a modified or gelled protein having desired cross-linking degree can be obtained by appropriately treating a substrate protein with the protein-deamidating enzyme to effect conversion of desired glutamine groups into glutamic acid residues and then subjecting the thus treated protein to the transglutaminase reaction.

It can also be used as a reagent for use in the functional modification of protein, namely for use in protein engineering. When the substrate protein is an enzyme, enzyme-chemical and physicochemical properties of the enzyme can be modified. For example, when an enzyme protein is deamidated by the enzyme of the invention, isoelectric point of the enzyme protein is reduced so that its pH stability can be modified. Also, other properties of the enzyme such as substrate affinity, substrate specificity, reaction rate, pH-dependency, temperature-dependency and temperature stability can be modified by changing the structure or electric environment of its active site.

It also can be used as reagents for analyses and studies of protein, such as a reagent for use in the determination of amide content of protein and a reagent for use in the solubilization of protein.

In addition, it can be used for the improvement of extraction and concentration efficiencies of cereal and bean proteins. In general, proteins of cereals and beans such as wheat and soybean are mostly insoluble in water and cannot therefore be extracted easily, but such proteins can be extracted easily and high content protein isolates can be obtained when these proteins are solubilized by treating a suspension of wheat flour or soybean flour with the enzyme of the invention.

In the case of soybean protein, when the protein is generally extracted from defatted soybean powder or flakes (protein content, about 50%), the protein is firstly insolubilized by a heat treatment, an ethanol treatment or an isoelectric point treatment at around pH 4.5, and then soluble polysaccharides are removed to obtain a soybean protein concentrate having a protein content of about 70%. When protein of more higher purity is desired, it is prepared by suspending or dissolving soybean powder or the concentrate in a dilute alkali solution to dissolve the protein and then removing insoluble substances. This product is called soybean protein isolate and contains about 90% of the protein. These soybean protein products are applied to various food articles such as ham, sausages and baby food, utilizing functions of soybean protein, such as emulsifying activity, gelling property and water-retaining property as well as its high nutritive value.

When the enzyme of the invention is used in producing these soybean protein products, not only the yield is improved due to the increased solubility of protein but also high concentration protein products can be produced. Since the protein products obtained in this manner are deamidated, they have excellent functionality. In consequence, they can exert excellent effects when used in various food articles such as meat or fish products and noodles, and their use renders possible production of food articles having new texture and functionality.

The following describes the protein-deamidating enzyme of the invention, a gene which encodes the protein-deamidating enzyme, a recombinant vector which contains the gene, a transformant transformed with the vector and a method for the production of the protein-deamidating enzyme, which comprises culturing the transformant in a medium, thereby allowing the transformant to produce the protein-deamidating enzyme, and subsequently collecting the protein-deamidating enzyme from the culture mixture.

Regarding the protein-deamidating enzyme of the invention, all of the protein-deamidating enzymes which can be obtained by the protein-deamidating enzyme production processes are included (i.e., allelic mutants and allelic variants are included), in which particularly preferred one is a polypeptide which has the amino acid sequence of SEQUENCE NO. 6 shown in the Sequence Listing attached, wherein one or more of amino acid residues of the amino acid sequence may be modified by at least one of deletion, addition, insertion and substitution, and more preferred one is a polypeptide which has the amino acid sequence of SEQUENCE NO. 6 shown in the Sequence Listing.

Examples of the gene which encodes the protein-deamidating enzyme of the present invention include a gene which can be obtained from a microorganism capable of producing the protein-deamidating enzyme by cloning of the gene and a gene which has a certain degree of homology with the gene. Regarding the homology, a gene having a homology of at least 60% or more, preferably a gene having a homology of 80% or more and more preferably a gene having a homology of 95% or more can be exemplified. The following nucleotide (polynucleotide; DNA or RNA) is desirable as the gene which encodes the protein-deamidating enzyme of the invention.

A nucleotide which comprises a nucleotide selected from the following nucleotides (a) to (g) and which encodes a polypeptide having the activity to deamidate amido groups in protein;
(a) a nucleotide which encode a polypeptide having the amino acid sequence of SEQUENCE NO. 6 shown in the Sequence Listing,
(b) a nucleotide which encode a polypeptide having the amino acid sequence of SEQUENCE NO. 6 shown in the Sequence Listing, wherein one or more of amino acid residues of the amino acid sequence are modified by at least one of deletion, addition, insertion and substitution,
(c) a nucleotide which has the nucleotide sequence of SEQUENCE NO. 5 shown in the Sequence Listing,
(d) a nucleotide which has the nucleotide sequence of SEQUENCE NO. 5 shown in the Sequence Listing, wherein one or more of bases of the nucleotide sequence are modified by at least one of deletion, addition, insertion and substitution,
(e) a nucleotide which hybridizes with any one of the above nucleotides (a) to (d) under a stringent condition,
(f) a nucleotide which has homology with any one of the above nucleotides (a) to (d), and
(g) a nucleotide which is degenerate with respect to any one of the above nucleotides (a) to (f).

The gene which encodes the protein-deamidating enzyme of the invention can be prepared from the microorganism capable of producing the protein-deamidating enzyme by carrying out cloning of the gene in the following manner. Firstly, the protein-deamidating enzyme of the invention is isolated and purified from a microorganism capable of producing the protein-deamidating enzyme by the aforementioned method and information on its partial amino acid sequence is obtained.

Regarding the determination method of a partial amino acid sequence, it is effective to carry out a method in which purified protein-deamidating enzyme is directly applied to an amino acid sequence analyzer (such as Protein Sequenser 476A, manufactured by Applied Biosystems) by Edman degradation method [*J. Biol. Chem.*, vol. 256, pp. 7990-7997 (1981)], or a method in which its limited hydrolysis is carried out using a proteolytic enzyme, the thus obtained peptide fragments are isolated and purified and then amino acid sequences of the thus purified peptide fragments are analyzed.

Based on the information of the thus obtained partial amino acid sequences, the protein-deamidating enzyme gene is cloned. In general, the cloning is carried out making use of a PCR method or a hybridization method.

When a hybridization method is used, the method described in [Molecular Cloning, A Laboratory Manual, edit. by T. Maniatis et al., Cold Spring Harbor Laboratory, 1989] may be used.

When a PCR method is used, the following method can be used.

Firstly, a gene fragment of interest is obtained by carrying out PCR reaction using genomic DNA of a microorganism capable of producing the protein-deamidating enzyme as the template and synthetic oligonucleotide primers designed based on the information of partial amino acid sequences. The PCR method is carried out in accordance with the method described in [PCR Technology, edit. by Erlich H. A., Stockton Press, 1989]. When nucleotide sequences of the thus amplified DNA fragments are determined by a usually used method such as the dideoxy chain termination method, a sequence which corresponds to the partial amino acid sequence of the protein-deamidating enzyme is found in the thus determined sequences, in addition to the sequences of synthetic oligonucleotide primers, so that a part of the protein-deamidating enzyme gene of interest can be obtained. As a matter of course, a gene which encodes complete protein-deamidating enzyme can be cloned by further carrying out a cloning method such as the hybridization method using the thus obtained gene fragment as a probe.

In Example 11 of this specification, a gene coding for the protein-deamidating enzyme was determined by the PCR method using *Chryseobacterium* sp. No. 9670. Complete nucleotide sequence of the gene coding for the protein-deamidating enzyme originated from *Chryseobacterium* sp. No. 9670 is shown in the SEQUENCE NO. 5, and the amino acid sequence encoded thereby was determined to be the sequence shown in the SEQUENCE NO. 6. In this connection, there are countless nucleotide sequences which correspond to the amino acid sequence shown in the SEQUENCE NO. 6, in addition to the nucleotide sequence shown in the SEQUENCE NO. 5, and all of these sequences are included in the scope of the invention.

The gene of interest can also be obtained by chemical synthesis based on the information of the amino acid sequence shown in the SEQUENCE NO. 6 and the nucleotide sequence shown in the SEQUENCE NO. 5 (cf., *Gene*, 60(1), 115-127 (1987)).

Regarding the protein-deamidating enzyme gene of the invention, a nucleotide which encodes a polypeptide having the amino acid sequence shown in SEQUENCE NO. 6, wherein one or more of amino acid residues of the amino acid sequence are modified by at least one of deletion, addition, insertion and substitution, a gene which hybridizes with the nucleotide under a stringent condition, a nucleotide which has homology with the nucleotide and a nucleotide which is degenerate with respective to the nucleotide are also included in the invention, with the proviso that the polypeptides encoded thereby have the protein-deamidating enzyme activity.

The term "under stringent condition" as used herein means the following condition. That is, a condition in which the reaction system is incubated at a temperature of from 50 to 65° C. for a period of from 4 hour to overnight in 6×SSC (1×SSC is a solution composed of 0.15 M NaCl and 0.015 M sodium citrate, pH 7.0) containing 0.5% SDS, 5×Denhart's [a solution composed of 0.1% bovine serum albumin (BSA), 0.1% polyvinyl pyrrolidone and 0.1% Ficoll 400] and 100 µg/ml of salmon sperm DNA.

By using the entire portion or a part of the protein-deamidating enzyme gene whose complete nucleotide sequence has been revealed making use of *Chryseobacterium* sp. No. 9670, as a probe for hybridization, DNA fragments having high homology with the protein-deamidating enzyme gene of SEQUENCE NO. 5 can be selected from genomic DNA libraries or cDNA libraries of microorganisms capable of producing other protein-deamidating enzymes.

The hybridization can be carried out under the aforementioned stringent condition. For example, a genomic DNA library or a cDNA library obtained from a microorganism capable of producing a protein-deamidating enzyme is fixed on a nylon membrane, and the thus prepared nylon membrane is subjected to blocking at 65° C. in a pre-hybridization solution containing 6×SSC, 0.5% SDS, 5× Denhart's and 100 µg/ml of salmon sperm DNA. Thereafter, each probe labeled with $^{32}$P is added to the nylon membrane which is then incubated overnight at 65° C. The thus treated nylon membrane is washed in 6×SSC at room temperature for 10 minutes, in 2×SSC containing 0.1% SDS at room temperature for 10 minutes and then in 0.2×SSC containing 0.1% SDS at 45° C. for 30 minutes, subsequently subjecting the thus washed membrane to an auto-radiography to detect a DNA fragment which specifically hybridizes with the probe. Also, genes which show various degree of homology can be obtained by changing certain conditions such as washing.

On the other hand, primers for use in the PCR reaction can be designed from the nucleotide sequence of the gene of the invention. By carrying out the PCR reaction using these primers, gene fragments having high homology with the gene of the invention can be detected and the complete gene can also be obtained.

In order to determine whether the thus obtained gene encodes a polypeptide having the protein-deamidating enzyme activity of interest, the thus determined nucleotide sequence is compared with the nucleotide sequence coding for the protein-deamidating enzyme of the invention or with its amino acid sequence, and the identity is estimated based on the gene structure and homology. Alternatively, it is possible to determine whether the gene encodes a polypeptide which has the protein-deamidating enzyme activity of interest by producing a polypeptide of the gene and measuring its protein-deamidating enzyme activity.

The following method is convenient for producing a polypeptide having the protein-deamidating enzyme activity using the protein-deamidating enzyme gene of the invention.

Firstly, transformation of a host is carried out using a vector containing the protein-deamidating enzyme gene of interest and then culturing of the thus obtained transformant is carried out under generally used conditions, thereby allowing the strain to produce a polypeptide having the protein-deamidating enzyme activity.

Examples of the host to be used include microorganisms, animal cells and plant cells. Examples of the microorganisms include bacteria such as *Escherichia coli* and other species belonging to the genera *Bacillus, Streptomyces* and *Lactococcus*, yeast species such as of the genera *Saccharomyces, Pichia* and *Kluyveromyces* and filamentous fungi such as of the genera *Aspergillus, Penicillium* and *Trichoderma*. Examples of the animal cells include those which utilize the baculovirus expression system.

Confirmation of the expression and expressed product can be made easily by the use of an antibody specific for the protein-deamidating enzyme, and the expression can also be confirmed by measuring the protein-deamidating enzyme activity.

As described in the foregoing, purification of the protein-deamidating enzyme from the transformant culture medium can be carried out by optional combination of centrifugation, UF concentration, salting out and various types of chromatography such as of ion exchange resins.

In addition, since the primary structure and gene structure of the protein-deamidating enzyme have been revealed by the invention, it is possible to obtain a gene coding for the amino acid sequence of a natural protein-deamidating enzyme, in which one or more of amino acid residues of the amino acid sequence are modified by at least one of deletion, addition, insertion and substitution, by introducing random mutation or site-specific mutation using the gene of the invention. This method renders possible preparation of a gene coding for a protein-deamidating enzyme which has the protein-deamidating enzyme activity but its properties such as optimum temperature, temperature stability, optimum pH, pH stability and substrate specificity are slightly changed, and it also renders possible production of such protein-deamidating enzymes by means of gene engineering techniques.

Examples of the method for introducing random mutation include a chemical DNA treating method in which a transition mutation is induced to convert cytosine base into uracil base by the action of sodium hydrogensulfite [*Proceedings of the National Academy of Sciences of the USA*, vol. 79, pp. 1408-1412 (1982)], a biochemical method in which base substitution is induced during the step of double strand formation in the presence of [α-S] dNTP [*Gene*, vol. 64, pp. 313-319 (1988)] and a PCR method in which PCR is carried out by adding manganese to the reaction system to decrease accuracy of the nucleotide incorporation [*Analytical Biochemistry*, vol. 224, pp. 347-353 (1995)].

Examples of the method for introducing site-specific mutation include a method in which amber mutation is employed [gapped duplex method; *Nucleic Acids Research*, vol. 12, no. 24, pp. 9441-9456 (1984)], a method in which recognition sites of restriction enzymes are used [*Analytical Biochemistry*, vol. 200, pp. 81-88 (1992); *Gene*, vol. 102, pp. 67-70 (1991)], a method in which mutation of dut (dUTPase) and ung (uracil DNA glycosylase) is used [Kunkel method; *Proceedings of the National Academy of Sciences of the USA*, vol. 82, pp. 488-492 (1985)], a method in which amber mutation is induced using DNA polymerase and DNA ligase [oligonucleotide-directed dual amber: ODA) method: *Gene*, vol. 152, pp. 271-275 (1995); JP-A-7-289262 (the term "JP-A" as used herein means an "unexamined published Japanese patent application")], a method in which a host introduced with a DNA repair system is used (JP-A-8-70874), a method in which a protein capable of catalyzing DNA chain exchange reaction is used (JP-A-8-140685), a method in which PCR is carried out using two different primers for mutation use to which recognition sites of restriction enzymes are added (U.S. Pat. No. 5,512,463), a method in which PCR is carried out using a double-stranded DNA vector having an inactivated drug resistance gene and two different primers [*Gene*, vol. 103, pp. 73-77 (1991)] and a method in which PCR is carried out making use of amber mutation (WO 98/02535).

Also, site-specific mutation can be introduced easily by the use of commercially available kits. Examples of such kits include Mutan™-G (manufactured by Takara Shuzo) in which the gapped duplex method is used, Mutan™-K (manufactured by Takara Shuzo) in which the Kunkel method is used, Mutan™-Express Km (manufactured by Takara Shuzo) in which the ODA method is used and QuickChange™ Site-Directed Mutagenesis Kit (manufactured by STRATAGENE) in which primers for mutation use and *Pyrococcus furiosus* DNA polymerase are used, as well as TaKaRa LA PCR in vitro Mutagenesis Kit (manufactured by Takara Shuzo) and Mutan™-Super Express Km (manufactured by Takara Shuzo) as kits in which PCR is used.

Thus, the primary structure and gene structure of the protein-deamidating enzyme provided by the invention render possible production of an inexpensive and high purity polypeptide having the protein-deamidating enzyme activity by means of gene engineering techniques.

In this connection, various literature and references are cited in the specification, and all of them are incorporated herein by references.

Examples of the present invention are given below by way of illustration and not by way of limitation. Unless otherwise noted, the term "%" used in the following means "W/V %"

EXAMPLE 1

Screening of Protein-Deamidating Enzyme Producing Strain a) Enrichment culturing: Each of 320 soil samples was inoculated into 5 ml of medium A containing Cbz-Gln-Gly as the sole nitrogen source and cultured at 30° C. for 6 days on a shaker. A 50 μl portion of the culture medium was inoculated in fresh medium A and again cultured at 30° C. for 3 days on a shaker. The culture broth was spread or streaked on a nutrient medium, and the grown bacterium or fungus was isolated as a single colony.

b) Plate selection: The thus obtained colonies were replicated on an agar medium comprised of the medium A and agar and cultured at 30° C. for 6 days, and the thus grown strains (150 bacterial strains and 294 fungal strains) were picked up.

c) Check of protein-deamidating enzyme productivity: Each of these strains was inoculated into a lactose liquid medium and cultured at 30° C. for 2 to 7 days on a shaker, and the culture broth was centrifuged to obtain culture supernatant. When protein-deamidating enzyme activity in these culture supernatant was measured, 50 bacterial strains and 85 fungal strains were positive.

Medium A: 0.1% Cbz-Gln-Gly, 0.5% glucose, 0.02% $KH_2PO_4$, 0.02% $MgSO_4.7H_2O$, 0.01% NaCl, 0.002% $CaCl_2$, 0.0002% $FeSO_4.7H_2O$, 0.0005% $NaMo_4.2H_2O$, 0.0005% $NaWO_4.4H_2O$, 0.0005% $MnSO_4.4H_2O$ and 0.01% $CuSO_4.5H_2O$ (pH 8.0)

Lactose liquid medium: 0.5% lactose, 1.0% peptone, 0.17% $Na_2HPO_4.H_2O$, 0.025% $KH_2PO_4$, 0.025% $MgSO_4.7H_2O$ and 0.005% $FeSO_4.7H_2O$ (pH 7.2, adjusted with 6 N NaOH).

EXAMPLE 2

From the 50 bacterial strains and 85 fungal strains obtained in Example 1, one strain (No. 9670) was selected to carry out the following test. As described in the specification, this was identified as a strain belonging to the genus *Chryseobacterium*.

*Chryseobacterium* sp. No. 9670 was cultured on a shaker at 25° C. for 64 hours using the aforementioned LB Base medium. Time course of the culturing is shown in Table 4.

TABLE 4

| Culture time (h) | pH | Growth | Enzyme activity (U/ml) |
|---|---|---|---|
| 18 | 8.24 | ++ | 0.116 |
| 40 | 8.65 | +++ | 0.224 |
| 64 | 9.41 | +++ | 0.201 |

EXAMPLE 3

From the 50 bacterial strains and 85 fungal strains obtained in Example 1, one strain (No. 9671) was selected to carry out the following test. This was also identified as a strain belonging to the genus *Chryseobacterium*. *Chryseobacterium* sp. No. 9671 was cultured in the same manner as described in Example 2. Protein-deamidating activity in the culture medium is shown in Table 5.

EXAMPLE 4

Each of *Chryseobacterium indologenes* IFO 14944, *Chryseobacterium meningosepticum* IFO 12535, *Chryseobacterium balustinum* IFO 15053, *Flavobacterium aquatile* IFO 15052, *Empedobacter brevis* IFO 14943, *Sphingobacterium spiritivorum* IFO 14948, *Sphingobacterium heparinum* IFO 12017, *Aureobacterium esteraromatidum* IFO and *Myroides odoratus* IFO 14945 was cultured in the same manner as described in Example 2. Protein-deamidating enzyme activity in each culture medium is shown in Table 5.

TABLE 5

| | | Deamidating activity (U/ml) | |
|---|---|---|---|
| Strain | Culture time (h) | Z-Gln-Gly | Casein |
| *Chryseobacterium* sp. No. 9671 | 24 | 0.160 | 0.143 |
| *Chryseobacterium gleum* JCM 2410 | 20 | 0.130 | 0.108 |
| *Chryseobacterium indologenes* IFO 14944 | 20 | 0.070 | 0.019 |
| *Chryseobacterium meningosepticum* IFO 12535 | 31 | 0.067 | 0.017 |
| *Chryseobacterium balustinum* IFO 15053 | 16 | 0.111 | 0.025 |
| *Flavobacterium aquatile* IFO 15052 | 48 | 0.019 | 0.038 |
| *Empedobacter brevis* IFO 14943 | 20 | 0.040 | 0.149 |
| *Sphingobacterium spiritivorum* IFO 14948 | 20 | 0.057 | 0.078 |
| *Sphingobacterium heparinum* IFO 12017 | 48 | 0.047 | 0.031 |
| *Aureobacterium esteraromatidum* IFO 3751 | 31 | 0.003 | 0.019 |
| *Myroides odoratus* IFO 14945 | 41 | 0.005 | 0.026 |

Production of protein-deamidating enzyme was confirmed in each strain.

EXAMPLE 5

When cultured in the same manner using M 17 medium (mfd. by Difco), Tryptone Soya medium (mfd. by Oxioid) or heart infusion medium (mfd. by Difco) instead of LB medium, production of the protein-deamidating enzyme was confirmed by all of the strains used in Examples 2 to 4.

EXAMPLE 6

The culture broth obtained after 40 hours of culturing in Example 2 was subjected to 20 minutes of centrifugation at 4° C. and at 12,000 rpm (22,200×g) to remove cells, and the thus obtained centrifugation supernatant was concentrated to about 25 times using an ultrafiltration membrane (SEP-0013, mfd. by Asahi Chemical Industry) and then freeze-dried to obtain a crude enzyme powder. This was dissolved in 10 mM sodium phosphate buffer solution (pH 6.5) containing 2.0 M NaCl, the thus formed insoluble matter was removed by 15 minutes of centrifugation at 4° C. and at 10,000 rpm (12,300× g), and the thus obtained centrifugation supernatant was applied to a Phenyl-Sepharose CL-6B column (mfd. by Pharmacia) which had been equilibrated with 10 mM sodium phosphate buffer solution (pH 6.5) containing 2.0 M NaCl, and the adsorbed protein was eluted by a linear. NaCl density gradient of from 2.0 M to 0 M.

Fractions having protein-deamidating activity were combined, concentrated using the ultrafiltration membrane and then applied to a Sephacryl S-100 column which had been equilibrated with 10 mM sodium phosphate buffer solution (pH 6.5) containing 0.6 M NaCl and 0.05% Tween 20, and the elution was carried out using the same buffer. Fractions having protein-deamidating activity were combined and concentrated using the ultrafiltration membrane to obtain a protein-deamidating enzyme solution. Results of the purification are shown in Table 2.

When the purified preparation of protein-deamidating enzyme obtained in this manner was subjected to 4 to 12%

SDS-polyacrylamide gel electrophoresis, this was confirmed to be a single protein having a molecular weight of 20 kDa as shown in the lane 2 of FIG. 1.

When measured by the aforementioned assay methods (the method which uses Z-Gln-Gly as the substrate and the method which uses casein as the substrate), the thus obtained enzyme preparation showed the activities of 33.7 units/ml (Z-Gln-Gly as the substrate) and 13.5 units/ml (casein as the substrate). Transglutaminase activity and protease activity were not detected.

EXAMPLE 7

Preparation of Deamidated Proteins

Figure 2:
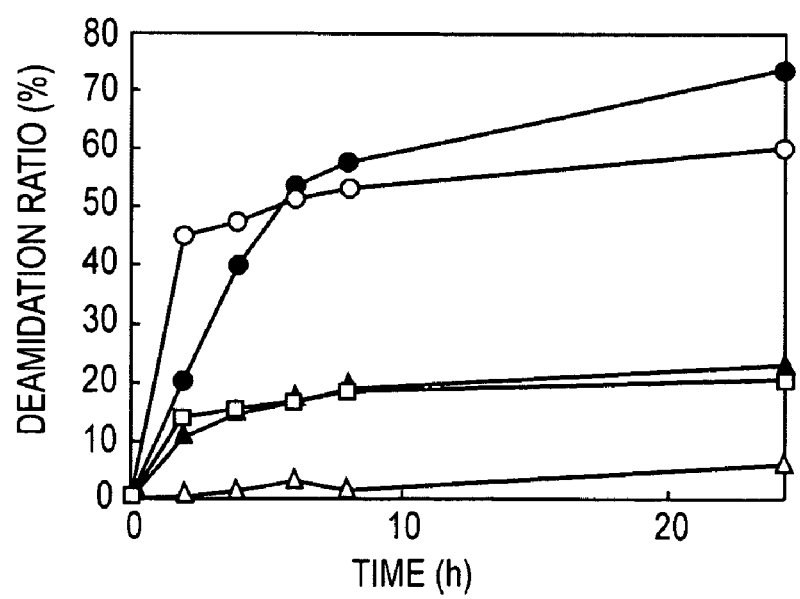
FIG. 2 is a graph showing time course of the changes in deamidation ratio of proteins of Example 7. Closed circle indicates wheat gluten, open circle indicates caseinate, closed triangle indicates whey protein, open square indicates albumen protein and open triangle indicates soybean protein.

A 1 g portion of wheat gluten, milk caseinate, whey protein, albumen protein or soybean protein was suspended in 100 ml of 100 mM sodium phosphate buffer (pH 6.5), 6.13 units of the protein-deamidating enzyme was added to the suspension and the mixture was allowed to undergo the enzyme reaction at 37° C. for 24 hours on a shaker. Time course of the changes in deamidation ratio during this reaction is shown in FIG. 2. The deamidation ratio was expressed as percentage of ammonia or ammonium released in the solution, determined after completion of the reaction, based on the total amido content in the protein. The total amido content in protein was obtained by hydrolyzing the protein (2% w/v) at 110° C. for 3 hours in 3 N sulfuric acid and determining amount of the released ammonia. It can be understood that the deamidation reaction was generated in the enzyme-added reaction system, because ammonia was released with the lapse of the reaction time, while release of ammonia was not observed in the reaction carried out in the absence of the enzyme as a control. The deamidation ratio was 74% in wheat gluten, 60% in caseinate, 23% in whey protein, 20% in soybean protein and 7% in albumen protein. After the reaction, this was heated at 75° C. for 15 minutes to terminate the reaction by deactivating the enzyme, dialyzed against water and then freeze-dried to obtain deamidated protein powder. Also, the reaction product obtained by carrying out in the absence of the enzyme as a control was treated in the same manner to obtain a control powder.

Figure 3:
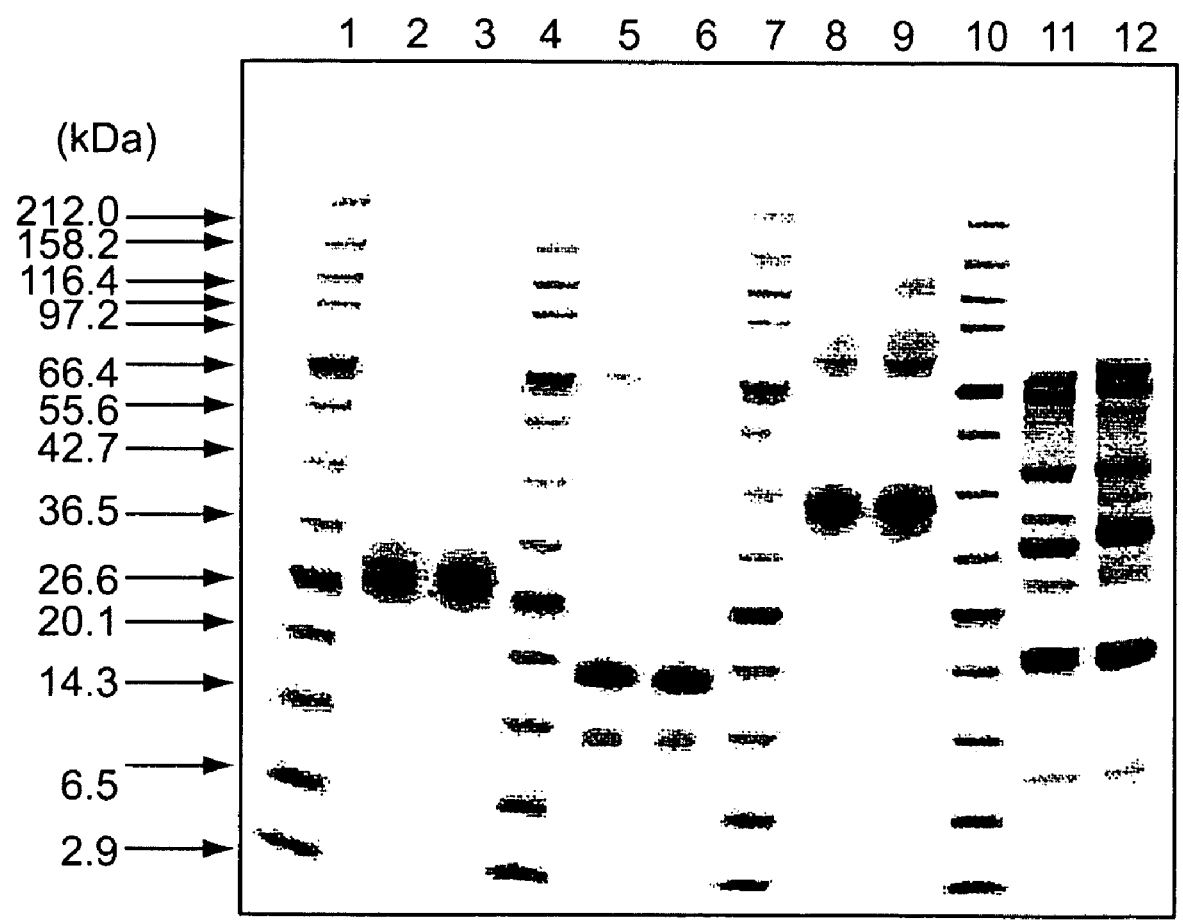
FIG. 3 is a graph showing results of SDS-polyacrylamide gel electrophoresis of the deamidated proteins of Example 7. Lanes 1, 4, 7 and 10 are molecular weight-marker proteins, lanes 2, 5, 8 and 11 are control caseinate, whey protein, albumen protein and soybean protein in that order and lanes 3, 6, 9 and 12 are deamidated caseinate, whey protein, albumen protein and soybean protein in that order.

FIG. 3 shows patterns of the 4 to 12% SDS-polyacrylamide gel electrophoresis of these deamidated proteins and control proteins. It can be understood that molecular weights of the deamidated proteins (lanes 3, 6, 9 and 12) were not changed in comparison with the enzyme-untreated control proteins, namely that both degradation of the proteins and increase in their molecular weight by cross-linking were not generated. In this case, although a slight shift of protein band was observed in the deamidated caseinate (lane 3) or soybean protein (lane 12) to higher molecular weight side, it is considered that this shift was due to the increase in minus charge in protein by deamidation, which caused reduction of its binding to SDS, also having minus charge, by electrostatic repulsion, and thereby resulted in the reduction of total minus charge of the protein-SDS complex in comparison with the non-deamidated protein, thus entailing reduced migration in the electrophoresis.

EXAMPLE 8

Improvement of Functionality (Foam Characteristics) of Deamidated Protein

Each of the deamidated protein powders obtained in Example 7 and enzyme-untreated protein powders obtained by the control test was dissolved in 10 mM phosphate buffer (pH 7.0) to a concentration of 0.5 mg/ml, and foamability and foam stability were measured by micro-conductivity method (Wilde P J, Colloid and Interface Science, 178, 733-739, 1996). The foam stability was expressed as the remaining degree of conductivity after 5 minutes. The results are shown in Table 6.

TABLE 6

| Protein | Foamability (%) | Foam stability (%) |
| --- | --- | --- |
| Control gluten | —* | 8.05 |
| Deamidated gluten | 1.25 | 41.44 |
| Control albumen protein | 1.50 | 33.96 |
| Deamidated albumen protein | 1.89 | 36.79 |
| Control soybean protein isolate | 1.84 | 42.96 |
| Deamidated soybean protein isolate | 2.81 | 63.19 |

*Not measurable due to considerably poor foamability.

Thus, it is evident that foam characteristics of protein can be sharply improved by deamidating the protein with the enzyme of the invention.

EXAMPLE 9

Improvement of functionality (Emulsifying Characteristics) of Deamidated Protein A 4 ml portion of solution of each of the deamidated protein powders obtained in Example 7 and enzyme-untreated protein powders obtained by the control test (1.0 mg/ml in 10 mM phosphate buffer (pH 7.0) and 1.0 g of corn oil (manufactured by Sigma) were put into a vial, pre-agitated for 1 minute using Vortex mixer and then passed five times through a single pass bulb homogenizer (EmulsiFlex-20000-B3, Avesten, Ottawa, Canada) under a high pressure (200 kPa), thereby preparing an oil/water emulsion. Particle distribution of the fresh emulsion was measured using a laser diffraction particle size analyzer (Coulter LS230, Coulter, Hialesh, Fla.). The emulsifying activity was expressed by specific surface area (surface area of particles per 1 ml of emulsion). Regarding the emulsifying stability, degrees of creaming, flocculation and coalescence which indicate disintegration of emulsion were observed with the naked eye after 7 days of standing at room temperature. Results of the emulsifying activity and emulsifying stability are shown in Tables 7 and 8, respectively.

TABLE 7

| Protein | Emulsifying activity (cm$^2$/ml) |
| --- | --- |
| Control gluten | 13,120 |
| Deamidated gluten | 57,531 |
| Control casein | 41,040 |
| Deamidated casein | 67,068 |
| Control whey protein | 29,534 |
| Deamidated whey protein | 29,996 |
| Control albumen protein | 37,252 |
| Deamidated albumen protein | 58,238 |
| Control soybean protein isolate | 16,512 |
| Deamidated soybean protein isolate | 30,796 |

TABLE 8

| Protein | Creaming | Flocculation | Coalescence |
| --- | --- | --- | --- |
| Control gluten | − | − | ++++++ |
| Deamidated gluten | − | − | + |
| Control casein | ++ | − | ± |
| Deamidated casein | + | − | ± |
| Control whey protein | +++ | − | − |
| Deamidated whey protein | +++ | − | − |
| Control albumen protein | ++++ | ++++ | − |
| Deamidated albumen protein | ++ | ± | − |
| Control soybean protein isolate | ++++ | + | + |
| Deamidated soybean protein isolate | ++ | + | ± |

Thus, it is evident that emulsifying activity and emulsifying stability of protein can be sharply improved by deamidating the protein with the enzyme of the invention.

EXAMPLE 10

Improvement of Functionality (Solubility) of Deamidated Protein

Each of the deamidated protein powders obtained in Example 7 and enzyme-untreated protein powders obtained by the control test was suspended and dissolved in 10 mM citrate-phosphate buffer having a pH value of from 2.7 to 6, 10 mM Tris-HCl buffer having a pH value of from 7 to 9 or an aqueous solution of pH 12 (adjusted with NaOH) to a concentration of 2.0 mg/ml, shaken at room temperature for 30 minutes and then allowed to stand at room temperature for 30 minutes. After measuring the pH value, this was centrifuged at a high speed of 16,000×g, the thus obtained supernatant was filtered through a 0.45 µm membrane and then the protein content in the filtrate was measured by the BCA method. Using the protein content in the filtrate as an index of solubility, the solubility at pH 12 was shown as 100% (Methods of Testing Protein Functionality, pp. 47-55, edited by G. M. Hall, Blackie Academic & Professional, London, 1996). The pH-solubility curves of deamidated proteins are shown in FIGS. 4 to 8.

Thus, it is evident that solubility of protein can be sharply improved by deamidating the protein with the enzyme of the invention.

Figure 4:
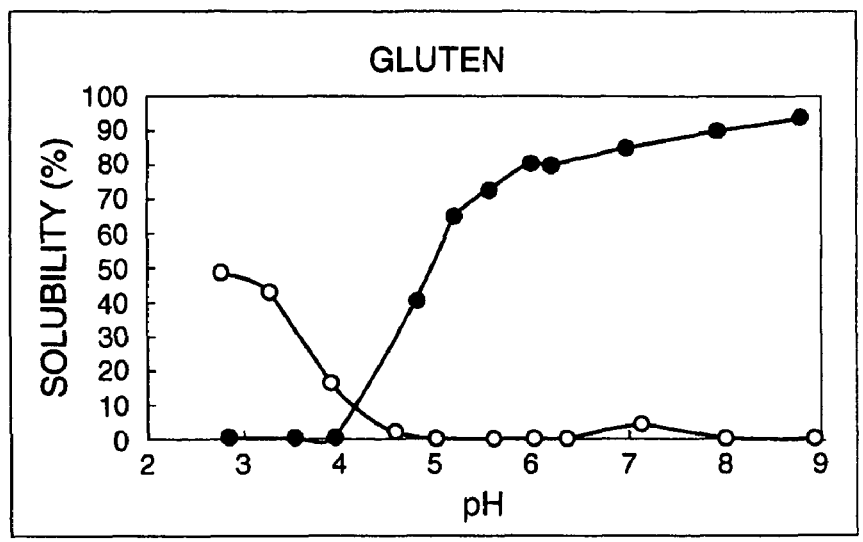
FIG. 4 is a graph showing pH-solubility curve of the deamidated gluten of Example 10. Closed circle indicates deamidated wheat gluten and open circle indicates control wheat gluten.
Figure 5:
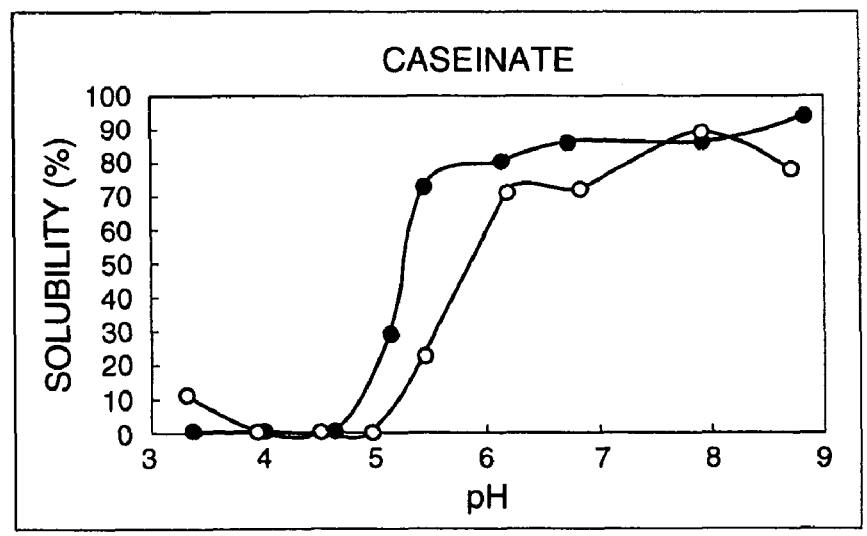
FIG. 5 is a graph showing pH-solubility curve of the deamidated caseinate of Example 10. Closed circle indicates deamidated caseinate and open circle indicates control caseinate.
Figure 6:
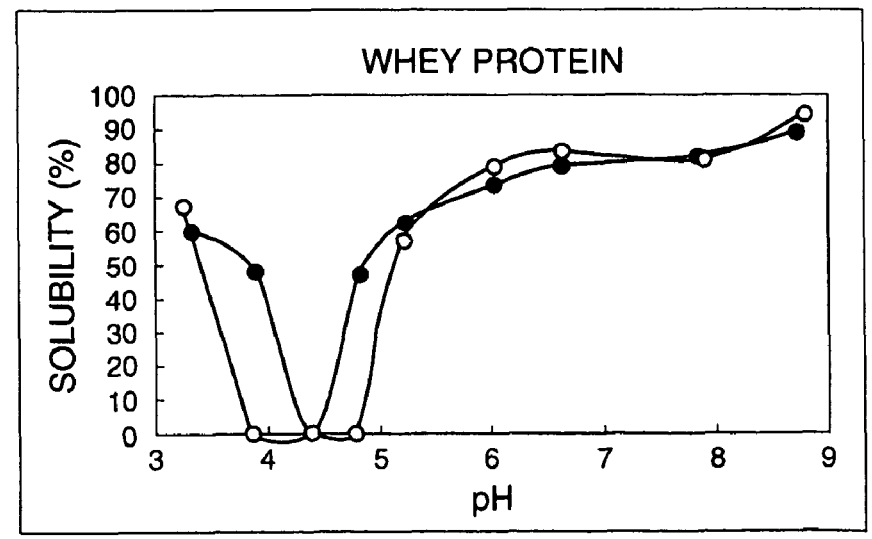
FIG. 6 is a graph showing pH-solubility curve of the deamidated whey protein of Example 10. Closed circle indicates deamidated whey protein and open circle indicates control whey protein.
Figure 7:
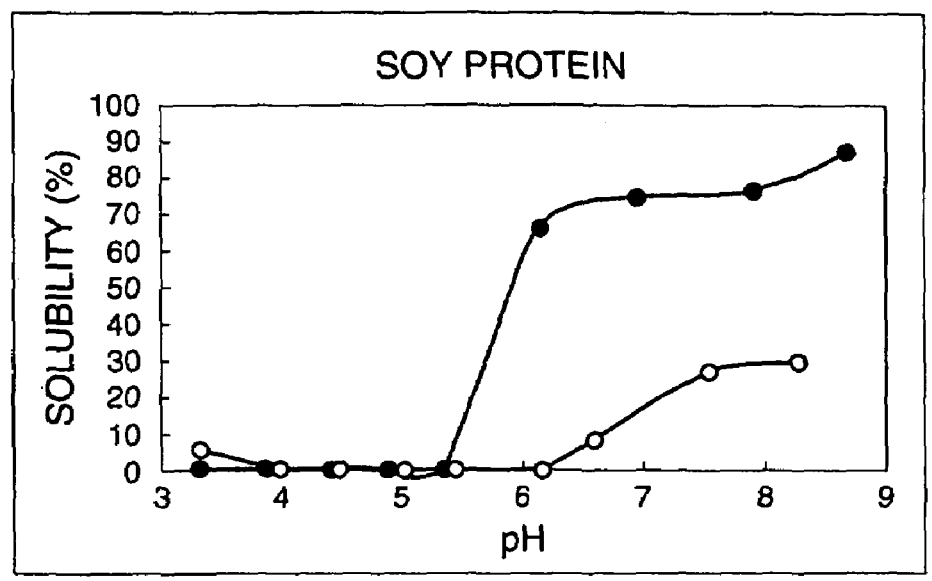
FIG. 7 is a graph showing pH-solubility curve of the deamidated soybean protein of Example 10. Closed circle indicates deamidated soybean protein and open circle indicates control whey protein.
Figure 8:
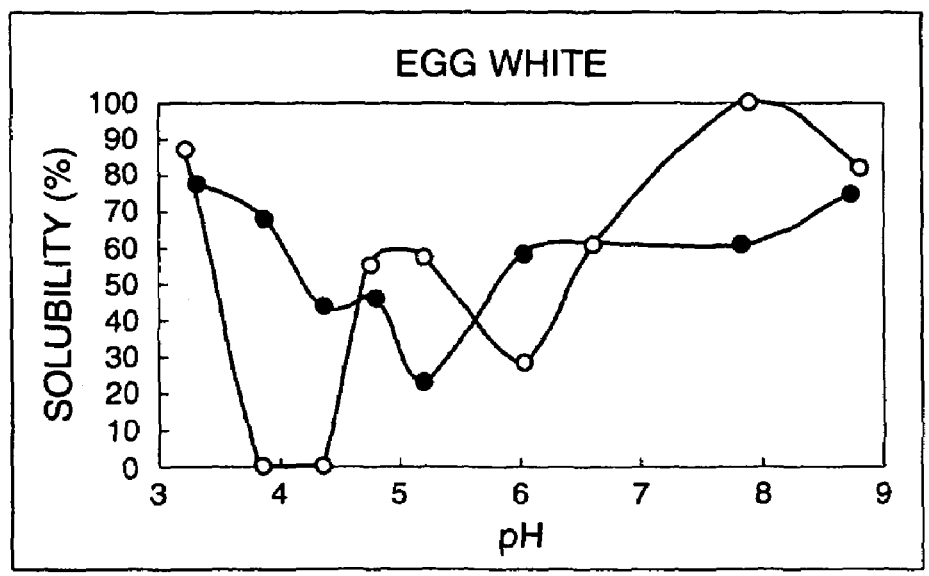
FIG. 8 is a graph showing pH-solubility curve of the deamidated albumen protein of Example 10. Closed circle indicates deamidated albumen protein and open circle indicates control albumen protein.

In the case of wheat gluten, the enzyme-untreated protein showed almost no solubility from pH 4.5 to about pH 9.0, while the deamidated wheat gluten showed about 40% solubility at pH 4.8 and 80% or more solubility at pH 6 or higher, which means remarkable improvements in the solubility (FIG. 4). In the case of caseinate, the enzyme-untreated caseinate showed low solubility at the weakly acidic range (pH 5 to pH 6) which is the pH of usual foods (e.g., 22% at pH 5.4). On the other hand, the deamidated caseinate showed about 30% solubility at pH 5.1 and about 70% or more solubility at pH 5.3 or higher (FIG. 5). In the case of whey protein, the enzyme-untreated protein showed no solubility from pH 3.8 to about pH 4.7, while the deamidated whey protein showed about 50% solubility at pH 3.9 and at pH 4.7 (FIG. 6). In the case of soybean protein, the solubility of the enzyme-untreated protein is generally low and showed only about 10% at pH 6.6 and about 30% at pH 7.5. On the other hand, the deamidated soybean protein showed 70% or more solubility at pH 6 or higher, which means remarkable improvements in the solubility (FIG. 7). In the case of egg protein, the enzyme-untreated protein showed no solubility from pH 3.9 to pH 4.3, while the deamidated protein showed about 70% solubility at pH 3.9 and about 43% solubility at pH 4.3 (FIG. 8).

EXAMPLE 11

Isolation of Gene Coding for the Protein-Deamidating Enzyme Derived from *Chryseobacterium* sp. No. 9670

In this specification, gene manipulation techniques were carried out in accordance with textbooks (e.g., "Molecular Cloning" 2nd ed., Cold Spring Harbor Laboratory Press, 1989) unless otherwise noted.

a) Isolation of Chromosomal DNA

A 4.5 ml portion of chromosomal DNA solution having a concentration of 210 µg/ml was obtained from 100-ml of culture broth in accordance with the method described in "Current Protocols in Molecular Biology", Unit 2.4 (John Wiley & Sons, Inc., 1994).

b) Determination of Partial Amino Acid Sequence

The purified protein-deamidating enzyme obtained in Example 3 was applied to a protein sequenser (mfd. by Applied Biosystems) to determine an N-terminal amino acid sequence of 20 residues shown in SEQUENCE NO. 1. Next, the purified protein-deamidating enzyme obtained in Example 3 was reduced and alkylated using performic acid and then hydrolyzed with trypsin. The thus obtained hydrolysate was applied to a reverse phase liquid chromatography, and one of the separated peptide fractions was applied to the protein sequenser to determine an internal amino acid sequence of 20 residues shown in SEQUENCE NO. 2.

```
SEQUENCE NO. 1:
Leu-Ala-Ser-Val-Ile-Pro-Asp-Val-Ala-Thr-Leu-Asn-
Ser-Leu-Phe-Asn-Gln-Ile-Lys-Asn

SEQUENCE NO. 2:
Ser-Pro-Ser-Asn-Ser-Tyr-Leu-Tyr-Asp-Asn-Asn-Leu-
Ile-Asn-Thr-Asn-Cys-Val-Leu-Thr
``` c) Preparation of DNA Probe by PCR

Based on the N-terminal region amino acid sequence and the internal amino acid sequence, the following two mixed oligonucleotides were synthesized using a DNA synthesizer (mfd. by Applied Biosystems) and used as PCR primers.

```
SEQUENCE NO. 3
Sense primer:
5'-GCI (TA) (CG) IGTIAT (TCA) CC (TACG) GA (TC) GT-3'          <N-1g>

SEQUENCE NO. 4
Antisense primer:
5'-A (AG) (AGTC) AC (AG) CA (AG) TT (AGTC) GT (AG) TT (AGT) AT-3'   <M-2a>
```

Using these primers and the *Chryseobacterium* sp. No. 9670 chromosomal DNA as the template, PCR reaction was carried out using Omnigene Thermal Cycler (mfd. by Hybaid) under the following conditions.

<PCR reaction solution>

| | |
|---|---|
| 10 × PCR reaction buffer (mfd. by Perkin Elmer) | 5.0 μl |
| dNTP mixture solution (each 2.5 mM, mfd. by Promega) | 4.0 μl |
| 20 μM sense primer | 10.0 μl |
| 20 μM antisense primer | 10.0 μl |
| distilled water | 20.25 μl |
| chromosomal DNA solution (190 μg/ml) | 0.5 μl |
| Taq DNA polymerase (mfd. by Perkin Elmer) | 0.25 μl |

<PCR reaction condition>

| | | |
|---|---|---|
| Stage 1: | denaturation (94° C., 5 minutes) | 1 cycle |
| Stage 2: | denaturation (94° C., 1 minute) | 30 cycles |
| | annealing (44° C., 1 minute) | |
| | elongation (72° C., 1 minute) | |
| Stage 3: | elongation (72° C., 10 minutes) | 1 cycle |

When the thus obtained DNA fragment of about 0.48 kb was cloned into pCRII (mfd. by Invitrogene) and then its nucleotide sequence was determined, a nucleotide sequence coding for the aforementioned partial amino acid sequence was found in a region just after the sense primer and just before the antisense primer. This DNA fragment was used as a DNA probe for use in the cloning of the complete gene.

d) Preparation of Gene Library

As a result of the Southern hybridization analysis of the *Chryseobacterium* sp. No. 9670 chromosomal DNA, a single band of about 4.9 kb capable of hybridizing with the probe DNA was found in an EcoRI digest. In order to carry out cloning of this EcoRI DNA fragment of about 4.9 kb, a gene library was prepared in the following manner. The chromosomal DNA prepared in the above step a) was digested with EcoRI, and the thus obtained digest was ligated to an EcoRI-treated λ ZAPII (mfd. by Stratagene) vector and packaged using Gigapack III Gold (mfd. by Stratagene) to obtain the gene library.

e) Screening of Gene Library

The 0.48 kb DNA fragment obtained in the above step c) was labeled using Megaprime DNA Labeling System (mfd. by Amersham) and $^{32}$P-α-dCTP. Using this as a probe, the gene library obtained in the above step d) was screened by plaque hybridization. Phage particles were recovered from the thus obtained positive plaques, and then a plasmid p9T1-2 containing an EcoRI fragment of about 4.5 kb was obtained by the in vivo excision method in accordance with the instruction provided by Stratagene.

f) Determination of Nucleotide Sequence

Nucleotide sequence of the plasmid p9T1-2 was determined in the conventional way. The nucleotide sequence which encodes the protein-deamidating enzyme is shown in SEQUENCE NO. 5. Also, amino acid sequence encoded by the SEQUENCE NO. 5 is shown in SEQUENCE NO. 6. The N-terminal region amino acid sequence (SEQUENCE NO. 1) and internal amino acid sequence (SEQUENCE NO. 2) determined in the above step b) were found in this amino acid sequence.

```
SEQUENCE NO. 5
TTTAAAACGATCCTGACAAAAGAAGTAAAAGGGCAAACCAATAAATTGGCGAGTGTAATT

CCTGATGTAGCTACATTAAATTCTTTATTCAATCAAATAAAGAATCAGTCTTGCGGTACC

TCTACGGCGTCCTCACCATGCATCACATTCAGATATCCTGTAGACGGATGTTATGCAAGA

GCCCATAAGATGAGACAAATCTTAATGAACAACGGCTATGACTGTGAAAAACAATTTGTA

TACGGAAACCTAAAGGCATCAACAGGAACTTGCTGTGTGGCGTGGAGCTACCACGTTGCA

ATATTGGTAAGCTATAAAAATGCTTCCGGAGTAACGGAAAAAAGAATTATTGATCCTTCA

CTATTTTCAAGCGGTCCTGTAACAGATACAGCATGGAGAAACGCTTGCGTTAACACCTCT

TGCGGATCTGCATCCGTTTCCTCTTATGCTTATACTGCAGGAAATGTTTATTACAGAAGT

CCTAGTAATTCTTACCTGTATGACAACAATCTGATCAATACCAACTGTGTACTGACTAAA

TTTTCACTGCTTTCCGGATGTTCTCCTTCACCTGCACCGGATGTATCCAGCTGTGGATTT
(555 bp)

SEQUENCE NO. 6
L A S V I P D V A T L N S L F N Q I K N

Q S C G T S T A S S P C I T F R Y P V D

G C Y A R A H K M R Q I L M N N G Y D C

E K Q F V Y G N L K A S T G T C C V A W

S Y H V A I L V S Y K N A S G V T E K R

I I D P S L F S S G P V T D T A W R N A

C V N T S C G S A S V S S Y A N T A G N

V Y Y R S P S N S Y L Y D N N L I N T N

C V L T K F S L L S G C S P S P A P D V

S S C G F
(185 amino acid)
```

The open reading frame of this gene is shown in SEQUENCE NO. 7. As shown in SEQUENCE NO. 7, the entire portion is encoded as a prepro protein having 320 amino acid residues, in which N-terminal 135 residues (underlined in SEQUENCE NO. 7) correspond to the prepro region and the remaining 185 residues correspond to the mature protein (cf. SEQUENCE NO. 6).

Among the 135 residues of the prepro region, the N-terminal 21 residues have the characteristics of the signal sequence and therefore are considered to be the pre region, and the remaining 114 residues are considered to be the pro region.

The invention is not particularly limited to polypeptides having protein-deamidating activity and nucleotides encoding the same, but also includes the longer polypeptides comprising the polypeptides having protein-deamidating activity (such as prepro proteins and pro proteins) and nucleotides encoding the same.

```
SEQUENCE NO. 7
AGTTAAAATAACCAACCAACTTAACAAAAACTCACCATTAAACTACAAATTACAATTATT

ATGAAAAATCTTTTTTTATCAATGATGGCCTTTGTGACCGTCTTAACTTTTAATTCCTGT
 M   K   N   L   F   L   S   M   M   A   F   V   T   V   L   T   F   N   S   C

GCCGATTCCAACGGGAATCAGGAAATCAACGGAAAGGAAAAACTAAGTGTAAATGATTCT
 A   D   S   N   G   N   Q   E   I   N   G   K   E   K   L   S   V   N   D   S

AAGCTGAAAGATTTCGGAAAGACTGTACCGGTAGGGATAGACGAAGAAAACGGAATGATA
 K   L   K   D   F   G   K   T   V   P   V   G   I   D   E   E   N   G   M   I

AAGGTGTCATTTATGTTAACTGCGCAATTCTATGAAATTAAGCCGACCAAAGAAAATGAG
 K   V   S   F   M   L   T   A   Q   F   Y   E   I   K   P   T   K   E   N   E

CAGTATATCGGAATGCTTAGACAGGCTGTTAAGAATGAATCTCCTGTACACATTTTCTTA
 Q   Y   I   G   M   L   R   Q   A   V   K   N   E   S   P   V   H   I   F   L

AAGCCTAATAGCAATGAAATAGGAAAAGTGGAGTCTGCAAGTCCGGAAGACGTAAGATAT
 K   P   N   S   N   E   I   G   K   V   E   S   A   S   P   E   D   V   R   Y

TTTAAAACGATCCTGACAAAAGAAGTAAAAGGGCAAACCAATAAATTGGCGAGTGTAATT
 F   K   T   I   L   T   K   E   V   K   G   Q   T   N   K   L   A   S   V   I

CCTGATGTAGCTACATTAAATTCTTTATTCAATCAAATAAAGAATCAGTCTTGCGGTACC
 P   D   V   A   T   L   N   S   L   F   N   Q   I   K   N   Q   S   C   G   T

TCTACGGCGTCCTCACCATGCATCACATTCAGATATCCTGTAGACGGATGTTATGCAAGA
 S   T   A   S   S   P   C   I   T   F   R   Y   P   V   D   G   C   Y   A   R

GCCCATAAGATGAGACAAATCTTAATGAACAACGGCTATGACTGTGAAAAACAATTTGTA
 A   H   K   M   R   Q   I   L   M   N   N   G   Y   D   C   E   K   Q   F   V

TACGGAAACCTAAAGGCATCAACAGGAACTTGCTGTGTGGCGTGGAGCTACCACGTTGCA
 Y   G   N   L   K   A   S   T   G   T   C   C   V   A   W   S   Y   H   V   A

ATATTGGTAAGCTATAAAAATGCTTCCGGAGTAACGGAAAAAAGAATTATTGATCCTTCA
 I   L   V   S   Y   K   N   A   S   G   V   T   E   K   R   I   I   D   P   S

CTATTTTCAAGCGGTCCTGTAACAGATACAGCATGGAGAAACGCTTGCGTTAACACCTCT
 L   F   S   S   G   P   V   T   D   T   A   W   R   N   A   C   V   N   T   S

TGCGGATCTGCATCCGTTTCCTCTTATGCTAATACTGCAGGAAATGTTTATTACAGAAGT
 C   G   S   A   S   V   S   S   Y   A   N   T   A   G   N   V   Y   Y   R   S

CCTAGTAATTCTTACCTGTATGACAACAATCTGATCAATACCAACTGTGTACTGACTAAA
 P   S   N   S   Y   L   Y   D   N   N   L   I   N   T   N   C   V   L   T   K

TTTTCACTGCTTTCCGGATGTTCTCCTTCACCTGCACCGGATGTATCCAGCTGTGGATTT
 F   S   L   L   S   G   C   S   P   S   P   A   P   D   V   S   S   C   G   F 320

TAATTAATTGATAATTTTACAGCACCTGCTCATTTACAGAATCAGCAGGTGCTGTTATAT
(1080)
*

SEQUENCE NO. 8
M K N L F L S M M A F V T V L T F N S C

A D S N G N Q E I N G K E K L S V N D S

K L K D F G K T V P V G I D E E N G M I

K V S F M L T A Q F Y E I K P T K E N E

Q Y I G M L R Q A V K N E S P V H I F L

K P N S N E I G K V E S A S P E D V R Y
```

-continued

FKTILTKEVKGQTNKLASVI

PDVATLNSLFNQIKNQSCGT

STASSPCITFRYPVDGCYAR

AHKMRQILMNNGYDCEKQFV

YGNLKASTGTCCVAWSYHVA

ILVSYKNASGVTEKRIIDPS

LFSSGPVTDTAWRNACVNTS

CGSASVSSYANTAGNVYYRS

PSNSYLYDNNLINTNCVLTK

FSLLSGCSPSPAPDVSSCGF
(320 amino acid)

EXAMPLE 12

Construction of Plasmid for Use in the Expression of Protein-Deamidating Enzyme in E. coli Based on the DNA sequences which encode the N-terminal region amino acid sequence and the C-terminal region amino acid sequence, the following two oligonucleotides were synthesized using a DNA synthesizer (mfd. by Applied Biosystems) and used as PCR primers.

Sequence No. 9

Sense primer for mature protein expression use:

SEQUENCE NO. 10
5'-CCGAATTCTTGGCGAGTGTAATTCCTGATG-3'

Sense primer for prepro protein expression use:

SEQUENCE NO. 11
5'-CAGAATTCATGAAAAATCTTTTTTTATCAATGGCC-3'

Antisense primer:

5'-TCGAATTCTTAAAATCCACAGCTGGATAC-3'

Using these primers and the protein-deamidating enzyme gene-containing plasmid p9T1-2 as the template, PCR reaction was carried out using Omnigene Thermal Cycler (mfd. by Hybaid) under the following conditions.

| <PCR reaction solution> | |
|---|---|
| 10 × PCR reaction buffer (mfd. by Perkin Elmer) | 10.0 μl |
| dNTP mixture solution (each 2.5 mM, mfd. by Promega) | 8.0 μl |
| 20 μM sense primer | 2.5 μl |
| 20 μM antisense primer | 2.5 μl |
| distilled water | 75.5 μl |
| plasmid p7T-1 solution (50 μg/ml) | 1.0 μl |
| Taq DNA polymerase (mfd. by Perkin Elmer) | 0.5 μl |
| <PCR reaction condition> | |
| Stage 1: denaturation (94° C., 5 minutes) | 1 cycle |
| Stage 2: denaturation (94° C., 1 minute) annealing (55° C., 1 minute) elongation (72° C., 1 minute) | 30 cycles |
| Stage 3: elongation (72° C., 10 minutes) | 1 cycle |

Each of the DNA fragment of about 0.57 kb obtained by the combination of sense primer for mature protein expression use with antisense primer and the DNA fragment of about 0.98 kb obtained by the combination of sense primer for prepro protein expression use with antisense primer was cloned into pCRII (mfd. by Invitrogen) to confirm that the nucleotide sequence was correct, and then the DNA fragment of about 0.57 kb and the DNA fragment of about 0.98 kb were recovered from these plasmids by EcoRI treatment. Each of these DNA fragments was inserted into EcoRI site of an expression vector pGEX-1λT for E. coli use (mfd. by Pharmacia), and the protein-deamidating enzyme-encoding DNA was connected to the C-terminal-corresponding side of the glutathione S transferase-encoding DNA contained in the pGEX-1λT, in the same direction, thereby obtaining a plasmid pN7-9 containing the DNA fragment coding for the mature protein and a plasmid pP3-9 containing the DNA fragment coding for the prepro protein. These plasmids can express a fusion protein of glutathione S transferase with protein-deamidating enzyme under control of tac promoter, and the protein-deamidating enzyme can be cut off from the fusion protein by thrombin treatment.

EXAMPLE 13

Expression of Protein-Deamidating Enzyme in E. coli

A transformant was obtained by introducing each of the expression plasmids pN7-9 and pP3-9 into E. coli BL21 (mfd. by Pharmacia). As a control, a transformant of E. coli BL21 having the expression vector pGEX-1λT was also obtained. Each of these transformants was cultured at 37° C. on a 200 rpm rotary shaker using LB medium containing 100 μg/ml of ampicillin, and the cells obtained at the logarithmic growth phase ($OD_{600}$=0.9-1.0) were mixed with 0.1 mM in final concentration of IPTG, cultured for 4 hours under the same conditions and then collected. The thus collected cells were suspended in 1/10 volume culture broth of 50 mM Tris-HCl (pH 8.0)/2 mM EDTA, mixed with 0.1 mg/ml in final concentration of egg white lysozyme and 0.1% in final concentration of Triton X-100 and allowed to stand at 30° C. for 15 minutes, and then the thus formed viscous DNA was sheared by mild ultrasonic treatment (3 cycles of 10 sec. on and 30 sec. off) to obtain a cell extract. A 100 μl portion of the cell extract was mixed with 4 μl of thrombin (1 U/μl in 9 mM sodium phosphate (pH 6.5)/140 mM NaCl) and allowed to stand at room temperature for 16 hours to obtain thrombin-treated cell extract. Also, a sample obtained by adding 4 μl of a buffer solution (9 mM sodium phosphate (pH 6.5)/140 mM NaCl) and carrying out the same reaction was used as a control of the thrombin treatment.

The protein-deamidating enzyme activity of the thus obtained samples was measured, with the results shown in Table 9.

TABLE 9

| Sample | Transformant | Thrombin treatment | Protein-deamidating activity (mU/ml) | |
|---|---|---|---|---|
| | | | Substrate: Z-Gln-Gly | Substrate: casein |
| 1 | E. coli BL21/pN7-9 | − | 31.10 | 16.99 |
| 2 | E. coli BL21/pN7-9 | + | 37.32 | 20.67 |
| 3 | E. coli BL21/pP3-9 | − | 1.05 | 2.75 |
| 4 | E. coli BL21/pP3-9 | + | 1.54 | 3.40 |
| 5 | E. coli BL21/pGEX-1λT | − | 0.00 | 0.00 |
| 6 | E. coli BL21/pGEX-1λT | + | 0.00 | 0.00 |

Thus, it is apparent that the E. coli strain having the mature protein-deamidating enzyme expression plasmid pN7-9 expresses the protein-deamidating activity. The E. coli strain having the prepro protein-deamidating enzyme expression plasmid pP3-9 also expressed the protein-deamidating activity though at a low level. On the contrary, expression of the protein-deamidating activity was not found in the control E. coli strain having the expression vector pGEX-1λT.

Separately, each of the samples 1, 2, 5 and 6 was subjected to 12% SDS-polyacrylamide gel electrophoresis to carry out Western blotting analysis using an antibody specific for the protein-deamidating enzyme. As a result, a band which reacted with the antibody was detected in the sample 1 at a position of about 43 Da in molecular weight which seemed to be a fusion protein of glutathione S transferase with the mature protein-deamidating enzyme, and a band was detected in the sample 2 at a position of about 20 kDa in molecular weight corresponding to the mature protein-deamidating enzyme, in addition to the band of about 43 Da in molecular weight. On the other hand, a band capable of reacting with the antibody was not detected in the samples 5 and 6.

On the basis of these results, it was confirmed that a recombinant protein-deamidating enzyme can be produced in E. coli using the protein-deamidating enzyme gene obtained by the invention.

A novel enzyme capable of acting upon amido groups in protein and thereby catalyzing the deamidation reaction, which was not found in the prior art, was found for the first time from a microorganism which is advantageous for industrial production. A broad range of applications are expected by this enzyme.

Also, since the primary structure and gene structure of the protein-deamidating enzyme were provided by the invention, inexpensive and high purity production of polypeptide having protein-deamidating enzyme activity by gene engineering techniques became possible.

While the invention has been described in detail and with reference to specific embodiments thereof, it will be apparent to one skilled in the art that various changes and modifications can be made therein without departing from the spirit and scope thereof.

This application is based on Japanese patent application No. Hei. 11-345044 filed on Dec. 3, 1999, both herein incorporated by reference.

What is claimed is:

1. An isolated polynucleotide which comprises a polynucleotide selected from the following nucleotides (a) to (d) and encoding a polypeptide having deamidating activity for amido groups in proteins;
   (a) a polynucleotide which encodes a polypeptide having the amino acid sequence of SEQ ID NO:6,
   (b) a polynucleotide which encodes a polypeptide having 95% sequence identity to the amino acid sequence of SEQ ID NO:6,
   (c) a polynucleotide which has the nucleotide sequence of SEQ ID NO:5, and
   (d) a polynucleotide which has at least 95% sequence identity to SEQ ID NO:5.

2. A polynucleotide which comprises a polynucleotide encoding a polypeptide having the amino acid sequence of SEQ ID NO:6.

3. A recombinant vector which contains the polynucleotide of claim 1.

4. A transformant transformed with the recombinant vector of claim 3.

5. A method for producing an enzyme having the activity to deamidate amido groups in protein, which comprises culturing the transformant of claim 4, thereby allowing said transformant to produce said enzyme, and subsequently collecting said enzyme from the culture.

6. A recombinant vector which contains the polynucleotide of claim 2.

7. A transformant transformed with the recombinant vector of claim 6.

8. A method for producing an enzyme having the activity to deamidate amido groups in protein, which comprises culturing the transformant of claim 7, thereby allowing said transformant to produce said enzyme, and subsequently collecting said enzyme from the culture.

\* \* \* \* \*

SEQUENCE LISTING

```
<160> NUMBER OF SEQ ID NOS: 11

<210> SEQ ID NO 1
<211> LENGTH: 20
<212> TYPE: PRT
<213> ORGANISM: Chryseobacterium sp. No. 9670

<400> SEQUENCE: 1

Leu Ala Ser Val Ile Pro Asp Val Ala Thr Leu Asn Ser Leu Phe Asn
1               5                   10                  15

Gln Ile Lys Asn
            20

<210> SEQ ID NO 2
<211> LENGTH: 20
<212> TYPE: PRT
<213> ORGANISM: Chryseobacterium sp. No. 9670

<400> SEQUENCE: 2

Ser Pro Ser Asn Ser Tyr Leu Tyr Asp Asn Asn Leu Ile Asn Thr Asn
1               5                   10                  15

Cys Val Leu Thr
            20

<210> SEQ ID NO 3
<211> LENGTH: 20
<212> TYPE: DNA
<213> ORGANISM: Artificial Sequence
<220> FEATURE:
```

```
<223> OTHER INFORMATION: sence primer
<220> FEATURE:
<221> NAME/KEY: misc_feature
<222> LOCATION: (3)..(3)
<223> OTHER INFORMATION: n = inosine
<220> FEATURE:
<221> NAME/KEY: misc_feature
<222> LOCATION: (6)..(6)
<223> OTHER INFORMATION: n = inosine
<220> FEATURE:
<221> NAME/KEY: misc_feature
<222> LOCATION: (9)..(9)
<223> OTHER INFORMATION: n = inosine
<220> FEATURE:
<221> NAME/KEY: misc_feature
<222> LOCATION: (15)..(15)
<223> OTHER INFORMATION: n = a, c, g or t

<400> SEQUENCE: 3
gcnwsngtna thccngaygt                                             20

<210> SEQ ID NO 4
<211> LENGTH: 20
<212> TYPE: DNA
<213> ORGANISM: Artificial Sequence
<220> FEATURE:
<223> OTHER INFORMATION: anti-sense primer
<220> FEATURE:
<221> NAME/KEY: misc_feature
<222> LOCATION: (3)..(3)
<223> OTHER INFORMATION: n = a, c, g or t
<220> FEATURE:
<221> NAME/KEY: misc_feature
<222> LOCATION: (12)..(12)
<223> OTHER INFORMATION: n = a, c, g or t

<400> SEQUENCE: 4
arnacrcart tngtrttdat                                             20

<210> SEQ ID NO 5
<211> LENGTH: 555
<212> TYPE: DNA
<213> ORGANISM: Chryseobacterium sp. No. 9670

<400> SEQUENCE: 5
ttggcgagtg taattcctga tgtagctaca ttaaattctt tattcaatca aataaagaat   60
cagtcttgcg gtacctctac ggcgtcctca ccatgcatca cattcagata tcctgtagac  120
ggatgttatg caagagccca taagatgaga caaatcttaa tgaacaacgg ctatgactgt  180
gaaaaacaat ttgtatacgg aaacctaaag gcatcaacag gaacttgctg tgtggcgtgg  240
agctaccacg ttgcaatatt ggtaagctat aaaaatgctt ccggagtaac ggaaaaagga  300
attattgatc cttcactatt ttcaagcggt cctgtaacag atacagcatg gagaaacgct  360
tgcgttaaca cctcttgcgg atctgcatcc gtttcctctt atgctaatac tgcaggaaat  420
gtttattaca gaagtcctag taattcttac ctgtatgaca caatctgat caataccaac   480 tgtgtactga ctaaattttc actgctttcc ggatgttctc cttcacctgc accggatgta  540
tccagctgtg gattt                                                  555

<210> SEQ ID NO 6
<211> LENGTH: 185
<212> TYPE: PRT
<213> ORGANISM: Chryseobacterium sp. No. 9670

<400> SEQUENCE: 6

Leu Ala Ser Val Ile Pro Asp Val Ala Thr Leu Asn Ser Leu Phe Asn
```

```
                1               5                   10                  15
Gln Ile Lys Asn Gln Ser Cys Gly Thr Ser Thr Ala Ser Ser Pro Cys
                20                  25                  30

Ile Thr Phe Arg Tyr Pro Val Asp Gly Cys Tyr Ala Arg Ala His Lys
        35                  40                  45

Met Arg Gln Ile Leu Met Asn Asn Gly Tyr Asp Cys Glu Lys Gln Phe
    50                  55                  60

Val Tyr Gly Asn Leu Lys Ala Ser Thr Gly Thr Cys Cys Val Ala Trp
65                  70                  75                  80

Ser Tyr His Val Ala Ile Leu Val Ser Tyr Lys Asn Ala Ser Gly Val
                85                  90                  95

Thr Glu Lys Arg Ile Ile Asp Pro Ser Leu Phe Ser Ser Gly Pro Val
                100                 105                 110

Thr Asp Thr Ala Trp Arg Asn Ala Cys Val Asn Thr Ser Cys Gly Ser
        115                 120                 125

Ala Ser Val Ser Ser Tyr Ala Asn Thr Ala Gly Asn Val Tyr Tyr Arg
        130                 135                 140

Ser Pro Ser Asn Ser Tyr Leu Tyr Asp Asn Asn Leu Ile Asn Thr Asn
145                 150                 155                 160

Cys Val Leu Thr Lys Phe Ser Leu Leu Ser Gly Cys Ser Pro Ser Pro
                165                 170                 175

Ala Pro Asp Val Ser Ser Cys Gly Phe
                180                 185

<210> SEQ ID NO 7
<211> LENGTH: 1080
<212> TYPE: DNA
<213> ORGANISM: Chryseobacterium sp. No. 9670
<220> FEATURE:
<221> NAME/KEY: CDS
<222> LOCATION: (61)..(1020)
<220> FEATURE:
<221> NAME/KEY: mat_peptide
<222> LOCATION: (466)..()

<400> SEQUENCE: 7
agttaaaata accaaccaac ttaacaaaaa ctcaccatta aactacaaat tacaattatt    60 atg aaa aat ctt ttt tta tca atg atg gcc ttt gtg acc gtc tta           105
Met Lys Asn Leu Phe Leu Ser Met Met Ala Phe Val Thr Val Leu
-135                -130                -125 act ttt aat tcc tgt gcc gat tcc aac ggg aat cag gaa atc aac           150
Thr Phe Asn Ser Cys Ala Asp Ser Asn Gly Asn Gln Glu Ile Asn
-120                -115                -110 gga aag gaa aaa cta agt gta aat gat tct aag ctg aaa gat ttc gga      198
Gly Lys Glu Lys Leu Ser Val Asn Asp Ser Lys Leu Lys Asp Phe Gly
-105                -100                -95                 -90 aag act gta ccg gta ggg ata gac gaa gaa aac gga atg ata aag gtg      246
Lys Thr Val Pro Val Gly Ile Asp Glu Glu Asn Gly Met Ile Lys Val
                -85                 -80                 -75 tca ttt atg tta act gcg caa ttc tat gaa att aag ccg acc aaa gaa      294
Ser Phe Met Leu Thr Ala Gln Phe Tyr Glu Ile Lys Pro Thr Lys Glu
            -70                 -65                 -60 aat gag cag tat atc gga atg ctt aga cag gct gtt aag aat gaa tct      342
Asn Glu Gln Tyr Ile Gly Met Leu Arg Gln Ala Val Lys Asn Glu Ser
        -55                 -50                 -45 cct gta cac att ttc tta aag cct aat agc aat gaa ata gga aaa gtg      390
Pro Val His Ile Phe Leu Lys Pro Asn Ser Asn Glu Ile Gly Lys Val
    -40                 -35                 -30
```

-continued

| | | |
|---|---|---|
| gag tct gca agt ccg gaa gac gta aga tat ttt aaa acg atc ctg aca<br>Glu Ser Ala Ser Pro Glu Asp Val Arg Tyr Phe Lys Thr Ile Leu Thr<br>-25                      -20                            -15                         -10 | 438 |
| aaa gaa gta aaa ggg caa acc aat aaa ttg gcg agt gta att cct gat<br>Lys Glu Val Lys Gly Gln Thr Asn Lys Leu Ala Ser Val Ile Pro Asp<br>               -5                          -1 1                               5 | 486 |
| gta gct aca tta aat tct tta ttc aat caa ata aag aat cag tct tgc<br>Val Ala Thr Leu Asn Ser Leu Phe Asn Gln Ile Lys Asn Gln Ser Cys<br>          10                           15                           20 | 534 |
| ggt acc tct acg gcg tcc tca cca tgc atc aca ttc aga tat cct gta<br>Gly Thr Ser Thr Ala Ser Ser Pro Cys Ile Thr Phe Arg Tyr Pro Val<br>      25                         30                         35 | 582 |
| gac gga tgt tat gca aga gcc cat aag atg aga caa atc tta atg aac<br>Asp Gly Cys Tyr Ala Arg Ala His Lys Met Arg Gln Ile Leu Met Asn<br>40                       45                         50                         55 | 630 |
| aac ggc tat gac tgt gaa aaa caa ttt gta tac gga aac cta aag gca<br>Asn Gly Tyr Asp Cys Glu Lys Gln Phe Val Tyr Gly Asn Leu Lys Ala<br>                  60                         65                         70 | 678 |
| tca aca gga act tgc tgt gtg gcg tgg agc tac cac gtt gca ata ttg<br>Ser Thr Gly Thr Cys Cys Val Ala Trp Ser Tyr His Val Ala Ile Leu<br>               75                           80                         85 | 726 |
| gta agc tat aaa aat gct tcc gga gta acg gaa aaa aga att att gat<br>Val Ser Tyr Lys Asn Ala Ser Gly Val Thr Glu Lys Arg Ile Ile Asp<br>      90                         95                         100 | 774 |
| cct tca cta ttt tca agc ggt cct gta aca gat aca gca tgg aga aac<br>Pro Ser Leu Phe Ser Ser Gly Pro Val Thr Asp Thr Ala Trp Arg Asn<br>105                      110                         115 | 822 |
| gct tgc gtt aac acc tct tgc gga tct gca tcc gtt tcc tct tat gct<br>Ala Cys Val Asn Thr Ser Cys Gly Ser Ala Ser Val Ser Ser Tyr Ala<br>120                      125                        130                   135 | 870 |
| aat act gca gga aat gtt tat tac aga agt cct agt aat tct tac ctg<br>Asn Thr Ala Gly Asn Val Tyr Tyr Arg Ser Pro Ser Asn Ser Tyr Leu<br>              140                         145                         150 | 918 |
| tat gac aac aat ctg atc aat acc aac tgt gta ctg act aaa ttt tca<br>Tyr Asp Asn Asn Leu Ile Asn Thr Asn Cys Val Leu Thr Lys Phe Ser<br>                  155                         160                        165 | 966 |
| ctg ctt tcc gga tgt tct cct tca cct gca ccg gat gta tcc agc tgt<br>Leu Leu Ser Gly Cys Ser Pro Ser Pro Ala Pro Asp Val Ser Ser Cys<br>170                      175                        180 | 1014 |
| gga ttt taattaattg ataattttac agcacctgct catttacaga atcagcaggt<br>Gly Phe<br>     185 | 1070 |
| gctgttatat | 1080 |

<210> SEQ ID NO 8
<211> LENGTH: 320
<212> TYPE: PRT
<213> ORGANISM: Chryseobacterium sp. No. 9670

<400> SEQUENCE: 8

Met  Lys Asn Leu Phe  Leu  Ser Met Met Ala Phe  Val Thr Val Leu
-135                  -130                          -125

Thr  Phe Asn Ser Cys  Ala  Asp Ser Asn Gly Asn  Gln Glu Ile Asn
-120                  -115                          -110

Gly  Lys Glu Lys Leu  Ser  Val Asn Asp Ser Lys  Leu Lys Asp Phe Gly
-105                  -100                      -95                     -90

Lys  Thr Val Pro Val  Gly  Ile Asp Glu Glu Asn  Gly Met Ile Lys Val
                       -85                         -80                        -75

Ser  Phe Met Leu Thr  Ala  Gln Phe Tyr Glu Ile  Lys Pro Thr Lys Glu

```
                -70                 -65                 -60
Asn Glu Gln Tyr Ile Gly Met Leu Arg Gln Ala Val Lys Asn Glu Ser
        -55                 -50                 -45

Pro Val His Ile Phe Leu Lys Pro Asn Ser Asn Glu Ile Gly Lys Val
    -40                 -35                 -30

Glu Ser Ala Ser Pro Glu Asp Val Arg Tyr Phe Lys Thr Ile Leu Thr
-25                 -20                 -15                 -10

Lys Glu Val Lys Gly Gln Thr Asn Lys Leu Ala Ser Val Ile Pro Asp
                -5                  -1  1                5

Val Ala Thr Leu Asn Ser Leu Phe Asn Gln Ile Lys Asn Gln Ser Cys
            10                  15                  20

Gly Thr Ser Thr Ala Ser Ser Pro Cys Ile Thr Phe Arg Tyr Pro Val
            25                  30                  35

Asp Gly Cys Tyr Ala Arg Ala His Lys Met Arg Gln Ile Leu Met Asn
40                  45                  50                  55

Asn Gly Tyr Asp Cys Glu Lys Gln Phe Val Tyr Gly Asn Leu Lys Ala
                60                  65                  70

Ser Thr Gly Thr Cys Cys Val Ala Trp Ser Tyr His Val Ala Ile Leu
            75                  80                  85

Val Ser Tyr Lys Asn Ala Ser Gly Val Thr Glu Lys Arg Ile Ile Asp
            90                  95                  100

Pro Ser Leu Phe Ser Ser Gly Pro Val Thr Asp Thr Ala Trp Arg Asn
    105                 110                 115

Ala Cys Val Asn Thr Ser Cys Gly Ser Ala Ser Val Ser Ser Tyr Ala
120                 125                 130                 135

Asn Thr Ala Gly Asn Val Tyr Tyr Arg Ser Pro Ser Asn Ser Tyr Leu
            140                 145                 150

Tyr Asp Asn Asn Leu Ile Asn Thr Asn Cys Val Leu Thr Lys Phe Ser
                155                 160                 165

Leu Leu Ser Gly Cys Ser Pro Ser Pro Ala Pro Asp Val Ser Ser Cys
        170                 175                 180

Gly Phe
   185

<210> SEQ ID NO 9
<211> LENGTH: 30
<212> TYPE: DNA
<213> ORGANISM: Artificial Sequence
<220> FEATURE:
<223> OTHER INFORMATION: sense primer

<400> SEQUENCE: 9
ccgaattctt ggcgagtgta attcctgatg                                      30

<210> SEQ ID NO 10
<211> LENGTH: 35
<212> TYPE: DNA
<213> ORGANISM: Artificial Sequence
<220> FEATURE:
<223> OTHER INFORMATION: sense primer

<400> SEQUENCE: 10
cagaattcat gaaaaatctt ttttatcaa tggcc                                 35

<210> SEQ ID NO 11
<211> LENGTH: 29
<212> TYPE: DNA
<213> ORGANISM: Artificial Sequence
```

```
<220> FEATURE:
<223> OTHER INFORMATION: anti-sense primer

<400> SEQUENCE: 11
tcgaattctt aaaatccaca gctggatac                                              29
```